United States Patent
Jonassen et al.

(10) Patent No.: US 7,615,532 B2
(45) Date of Patent: Nov. 10, 2009

(54) INSULIN DERIVATIVES

(75) Inventors: Ib Jonassen, Valby (DK); Thomas Hoeg-Jensen, Klampenborg (DK); Svend Havelund, Bagsværd (DK); Ulla Ribel-Madsen, Virum (DK); Tina Møller Tagmose, Ballerup (DK); Peter Madsen, Bagsværd (DK)

(73) Assignee: Novo Nordisk A/S, Bagsvaerd (DE)

( * ) Notice: Subject to any disclaimer, the term of this patent is extended or adjusted under 35 U.S.C. 154(b) by 316 days.

(21) Appl. No.: 11/343,005

(22) Filed: Jan. 30, 2006

(65) Prior Publication Data

US 2006/0183668 A1    Aug. 17, 2006

Related U.S. Application Data

(63) Continuation of application No. PCT/DK2004/000511, filed on Jul. 22, 2004.

(60) Provisional application No. 60/495,451, filed on Aug. 14, 2003.

(30) Foreign Application Priority Data

Aug. 5, 2003    (DK)    ............... 2003 01129

(51) Int. Cl.
    *A61K 38/28*    (2006.01)
(52) U.S. Cl. .......................................... 514/3; 530/303

(58) Field of Classification Search ...................... None
See application file for complete search history.

(56) References Cited

U.S. PATENT DOCUMENTS

| | | | |
|---|---|---|---|
| 3,528,960 | A | 9/1970 | Haas |
| 5,898,067 | A | 4/1999 | Balschmidt et al. |
| 6,251,856 | B1 | 6/2001 | Markussen et al. |
| 2002/0045731 | A1 | 4/2002 | Schaffer et al. |

FOREIGN PATENT DOCUMENTS

| | | | |
|---|---|---|---|
| EP | 894095 | | 2/1997 |
| EP | 0894095 | * | 2/1999 |
| GB | 1492997 | | 7/1976 |
| WO | 91/12817 | | 2/1991 |
| WO | 95/07931 | | 9/1994 |
| WO | 98/02460 | | 7/1997 |

* cited by examiner

*Primary Examiner*—Christopher R. Tate
*Assistant Examiner*—Roy Teller
(74) *Attorney, Agent, or Firm*—Shelby J. Walker

(57) ABSTRACT

The present invention relates to insulin derivatives which are naturally occurring insulins or analogues thereof which have a side chain attached either to the α-amino group of the N-terminal amino acid residue of the B chain or to the ε-amino group of a Lys residue present in the B chain of the parent insulin, the side chain being of the general formula:

-W-X—Y-Z wherein W, X, Y and Z are as defined in the disclosure.

12 Claims, No Drawings

INSULIN DERIVATIVES

CROSS-REFERENCE TO RELATED APPLICATIONS

This application is a continuation of International Application No. PCT/DK2004/000511, filed Jul. 22, 2004, which claims priority from Danish Patent Application No. PA 2003 01129 filed Aug. 5, 2003 and to U.S. Patent Application No. 60/495,451 filed Aug. 14, 2003.

FIELD OF THE INVENTION

The present invention relates to novel human insulin derivatives which are soluble at physiological pH values and have a prolonged profile of action. The invention also relates to methods of providing such derivatives, to pharmaceutical compositions containing them, to a method of treating diabetes and hyperglycemia using the insulin derivatives of the invention and to the use of such insulin derivatives in the treatment of diabetes and hyperglycemia.

BACKGROUND OF THE INVENTION

Currently, the treatment of diabetes, both type 1 diabetes and type 2 diabetes, relies to an increasing extent on the so-called intensive insulin treatment. According to this regimen, the patients are treated with multiple daily insulin injections comprising one or two daily injections of a long acting insulin to cover the basal insulin requirement supplemented by bolus injections of a rapid acting insulin to cover the insulin requirement related to meals.

Long acting insulin compositions are well known in the art. Thus, one main type of long acting insulin compositions comprises injectable aqueous suspensions of insulin crystals or amorphous insulin. In these compositions, the insulin compounds utilized typically are protamine insulin, zinc insulin or protamine zinc insulin.

Certain drawbacks are associated with the use of insulin suspensions. Thus, in order to secure an accurate dosing, the insulin particles must be suspended homogeneously by gentle shaking before a defined volume of the suspension is withdrawn from a vial or expelled from a cartridge. Also, for the storage of insulin suspensions, the temperature must be kept within more narrow limits than for insulin solutions in order to avoid lump formation or coagulation.

While it was earlier believed that protamines were non-immunogenic, it has now turned out that protamines can be immunogenic in man and that their use for medical purposes may lead to formation of antibodies. Also, evidence has been found that the protamine-insulin complex is itself immunogenic. Therefore, with some patients the use of long acting insulin compositions containing protamines must be avoided.

Another type of long acting insulin compositions are solutions having a pH value below physiological pH from which the insulin will precipitate because of the rise in the pH value when the solution is injected. A drawback with these solutions is that the particle size distribution of the precipitate formed in the tissue on injection, and thus the release profile of the medication, depends on the blood flow at the injection site and other parameters in a somewhat unpredictable manner. A further drawback is that the solid particles of the insulin may act as a local irritant causing inflammation of the tissue at the site of injection.

WO 91/12817 (Novo Nordisk ANS) discloses soluble insulin compositions comprising insulin complexes of cobalt(III). The action profile of these complexes is only moderately prolonged and the bioavailability is reduced relative to human insulin.

Human insulin has three primary amino groups: the N-terminal group of the A-chain and of the B-chain and the ε-amino group of $Lys^{B29}$. Several insulin derivatives which are substituted in one or more of these groups are known in the prior art. Thus, U.S. Pat. No. 3,528,960 (Eli Lilly) relates to N-carboxyaroyl insulins in which one, two or three primary amino groups of the insulin molecule has a carboxyaroyl group.

According to GB Patent No. 1.492.997 (Nat. Res. Dev. Corp.), it has been found that insulin with a carbamyl substitution at $N^{\epsilon B29}$ has an improved profile of hypoglycaemic effect.

JP laid-open patent application No. 1-254699 (Kodama Co., Ltd.) discloses insulin wherein a fatty acid is bound to the amino group of $Phe^{B1}$ or to the ε-amino group of $Lys^{B29}$ or to both of these. The stated purpose of the derivatisation is to obtain a pharmacologically acceptable, stable insulin preparation.

Insulins, which in the B30 position have an amino acid having at least five carbon atoms which cannot necessarily be coded for by a triplet of nucleotides, are described in JP laid-open patent application No. 57-067548 (Shionogi). The insulin analogues are claimed to be useful in the treatment of diabetes mellitus, particularly in patients who are insulin resistant due to generation of bovine or porcine insulin antibodies.

WO 95/07931 (Novo Nordisk A/S) discloses human insulin derivatives wherein the ε-amino group of $LyS^{B29}$ has a lipophilic substituent. These insulin derivatives have a prolonged profile of action and are soluble at physiological pH values.

EP 894095 discloses insulin derivatives wherein the N-terminal group of the B-chain and/or the ε-amino group of Lys in position B28, B29 or B30 has a substituent of the formula —CO—W—COOH where W can be a long chain hydrocarbon group. These insulin derivatives have a prolonged profile of action and are soluble at physiological pH values.

However, there is still a need for insulins having a more prolonged profile of action than the insulin derivatives known up till now and which at the same time are soluble at physiological pH values and have a potency which is comparable to that of human insulin.

SUMMARY OF THE INVENTION

The present invention is based on the recognition that the overall hydrophobicity of an insulin derivative molecule plays an important role for the in vivo potency of the derivative.

In one aspect the present invention relates to an insulin derivative which is a naturally occurring insulin or an analogue thereof which has a side chain attached either to the α-amino group of the N-terminal amino acid residue of the B chain or to the ε-amino group of a Lys residue present in the B chain of the parent insulin, the side chain being of the general formula:

-W-X—Y-Z wherein W is:
  an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin;

a chain composed of two, three or four α-amino acid residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or a covalent bond from X to the α-amino group of the N-terminal amino acid residue of the B chain or to the ε-amino group of a Lys residue present in the B chain of the parent insulin;

X is:
—$\underline{C}$O—;
—CH(COOH) $\underline{C}$O—;
—N(CH$_2$COOH)CH$_2\underline{C}$O—;
—N(CH$_2$COOH)CH$_2$CON(CH$_2$COOH)CH$_2\underline{C}$O—;
—N(CH$_2$CH$_2$COOH)CH$_2$CH$_2\underline{C}$O—;
—N(CH$_2$CH$_2$COOH)CH$_2$CH$_2$CON(CH$_2$CH$_2$COOH)CH$_2$CH$_2\underline{C}$O—;
—NHCH(COOH)(CH$_2$)$_4$NH$\underline{C}$O—;
—N(CH$_2$CH$_2$COOH)CH$_2\underline{C}$O—; or
—N(CH$_2$COOH)CH$_2$CH$_2\underline{C}$O—.

that
a) when W is an amino acid residue or a chain of amino acid residues, via a bond from the underscored carbonyl carbon forms an amide bond with an amino group in W, or
b) when W is a covalent bond, via a bond from the underscored carbonyl carbon forms an amide bond with the N-terminal α-amino group in the B chain or with the ε-amino group of a Lys residue present in the B chain of the parent insulin;

Y is:
—(CH$_2$)$_m$— where m is an integer in the range of 6 to 32;
a divalent hydrocarbon chain comprising 1, 2 or 3 -CH=CH— groups and a number of —CH$_2$— groups sufficient to give a total number of carbon atoms in the chain in the range of 10 to 32;
a divalent hydrocarbon chain of the formula —(CH$_2$)$_v$C$_6$H$_4$(CH$_2$)$_w$— wherein v and w are integers or one of them is zero so that the sum of v and w is in the range of 6 to 30; and Z is:
—COOH;
—CO-Asp;
—CO-Glu;
—CO-Gly;
—CO-Sar;
—CH(COOH)$_2$;
—N(CH$_2$COOH)$_2$;
—SO$_3$H; or
—PO$_3$H;

and any Zn$^{2+}$ complexes thereof, provided that when W is a covalent bond and X is —CO—, then Z is different from —COOH.

In one embodiment of the invention, the side chain -W-X—Y-Z is attached to the α-amino group of the N-terminal amino acid residue of the B chain of the parent insulin.

In another embodiment of the invention, side chain -W-X—Y-Z is attached to the ε-amino group of a Lys residue present in the B chain of the parent insulin. In one more specific aspect of this embodiment, the side chain —W13 X—Y-Z is attached to the ε-amino group of a Lys residue present in position 28 of the B chain. In a further more specific aspect of this embodiment, the side chain -W-X—Y-Z is attached to the ε-amino group of a Lys residue present in position 29 of the B chain. In a further more specific aspect of this embodiment, the side chain -W-X—Y-Z is attached to the ε-amino group of a Lys residue present in position 30 of the B chain.

The substructure W of the side chain -W-X—Y-Z can be a covalent bond. Alternatively, W can be a residue of an α-amino acid having a carboxylic acid group in the side chain and comprising a total of from 4 to 10 carbon atoms. Specifically, W can be the residue of an α-amino acid, that can be coded for by the genetic code. Thus, W can, for example, be selected from the group consisting of α-Asp, β-Asp, α-Glu, and γ-Glu. Further options for W are for example α-hGlu and δ-hGlu.

In a further embodiment, W is a chain composed of two α-amino acid residues of which one has from 4 to 10 carbon atoms and a carboxylic acid group in the side chain while the other has from 2 to 11 carbon atoms but no free carboxylic acid group. The α-amino acid residue with no free carboxylic acid group can be a neutral, codable α-amino acid residue. Examples of W according to this embodiment are: α-Asp-Gly; Gly-α-Asp; β-Asp-Gly; Gly-β-Asp; α-Glu-Gly; Gly-α-Glu; γ-Glu-Gly; Gly-γ-Glu; α-hGlu-Gly; Gly-α-hGlu; δ-hGlu-Gly; and Gly-δ-hGlu.

In a further embodiment, W is a chain composed of two α-amino acid residues, independently having from 4 to 10 carbon atoms, and both having a carboxylic acid group in the side chain. One of these α-amino acid residues or both of them can be codable α-amino acid residues. Examples of W according to this embodiment are: α-Asp-α-Asp; α-Asp-α-Glu; α-Asp-α-hGlu; α-Asp-β-Asp; α-Asp-γ-Glu; α-Asp-δ-hGlu; β-Asp-α-Asp; β-Asp-α-Glu; β-Asp-α-hGlu; β-Asp-β-Asp; β-Asp-γ-Glu; β-Asp-δ-hGlu; α-Glu-α-Asp; α-Glu-α-Glu; α-Glu-α-hGlu; α-Glu-β-Asp; α-Glu-γ-Glu; α-Glu-δ-hGlu; γ-Glu-α-Asp; γ-Glu-α-Glu; γ-Glu-α-hGlu; γ-Glu-β-Asp; γ-Glu-γ-Glu; γ-Glu-δ-hGlu; α-hGlu-α-Asp; α-hGlu-α-Glu; α-hGlu-α-hGlu; α-hGlu-β-Asp; α-hGlu-γ-Glu; α-hGlu-δ-hGlu; δ-hGlu-α-Asp; δ-hGlu-α-Glu; δ-hGlu-α-hGlu; δ-hGlu-β-Asp; δ-hGlu-γ-Glu; and δ-hGlu-δ-hGlu.

In a further embodiment, W is a chain composed of three α-amino acid residues, independently having from 4 to 10 carbon atoms, the amino acid residues of the chain being selected from the group of residues having a neutral side chain and residues having a carboxylic acid group in the side chain so that the chain has at least one residue which has a carboxylic acid group in the side chain. In one embodiment, the amino acid residues are codable residues.

In a further embodiment, W is a chain composed of four α-amino acid residues, independently having from 4 to 10 carbon atoms, the amino acid residues of the chain being selected from the group having a neutral side chain and residues having a carboxylic acid group in the side chain so that the chain has at least one residue which has a carboxylic acid group in the side chain. In one embodiment, the amino acid residues are codable residues.

In one embodiment W can be connected to the ε-amino group of the Lys residue in the B-chain via an urea derivative.

The substructure X of the side chain -W-X—Y-Z can be a group of the formula —$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —CH(COOH)$\underline{CO}$— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —N(CH$_2$COOH)CH$_2$$\underline{CO}$— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —N(CH$_2$CH$_2$COOH)CH$_2$$\underline{CO}$— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —N(CH$_2$COOH)CH$_2$CH$_2$$\underline{CO}$— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —N(CH$_2$COOH)CH$_2$CON(CH$_2$COOH)CH$_2$$\underline{CO}$— that, via a bond from the underscored carbonyl carbon, forms an amide bond with an amino group in W or, when W is a covalent bond, with the N-terminal α-amino group in the B chain or with the f-amino group of a Lys residue present in the B chain of the parent insulin.

In a further embodiment, the substructure X of the side chain can be a group of the formula —N(CH$_2$CH$_2$COOH)CH$_2$CH$_2$$\underline{CO}$— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —N(CH$_2$CH$_2$COOH)CH$_2$CH$_2$CON(CH$_2$CH$_2$COOH)CH$_2$CH$_2$$\underline{CO}$— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

The substructure Y of the side chain -W-X—Y-Z can be a group of the formula —(CH$_2$)$_m$— where m is an integer in the range of from 6 to 32, from 8 to 20, from 12 to 20, or from 12-16.

In another embodiment, Y is a divalent hydrocarbon chain comprising 1, 2 or 3 —CH=CH— groups and a number of —CH$_2$— groups sufficient to give a total number of carbon atoms in the chain in the range of from 6 to 32, from 10 to 32, from 12 to 20, or from 12-16.

In another embodiment, Y is a divalent hydrocarbon chain of the formula —(CH$_2$)$_v$C$_6$H$_4$(CH$_2$)$_w$— wherein v and w are integers or one of them is zero so that the sum of v and w is in the range of from 6 to 30, from 10 to 20, or from 12-16.

In one embodiment, the substructure Z of the side chain -W-X—Y-Z is —COOH provided that when W is a covalent bond and X is —CO—, then Z is different from —COOH.

In another embodiment, Z is —CO-Asp.
In another embodiment, Z is —CO-Glu.
In another embodiment, Z is —CO-Gly.
In another embodiment, Z is —CO-Sar.
In another embodiment, Z is —CH(COOH)$_2$.
In another embodiment, Z is —N(CH$_2$COOH)$_2$.
In another embodiment, Z is —SO$_3$H.
In another embodiment, Z is —PO$_3$H.

In a further embodiment W is selected from the group consisting of α-Asp, β-Asp, α-Glu, and γ-Glu; X is —CO— or —CH(COOH)CO; Y is —(CH$_2$)$_m$— where m is an integer in the range of 12-18 and Z is —COOH or —CH(COOH)$_2$.

The insulin moiety—in the present text also referred to as the parent insulin—of an insulin derivative according to the invention can be a naturally occurring insulin such as human insulin or porcine insulin. Alternatively, the parent insulin can be an insulin analogue.

In one group of parent insulin analogues, the amino acid residue at position A21 is Asn.

In another group of parent insulin analogues, the amino acid residue at position A21 is Gly. Specific examples from this group of analogues are Gly$^{A21}$ human insulin, Gly$^{A21}$ des(B30) human insulin; and Gly$^{A21}$Arg$^{B31}$Arg$^{B32}$ human insulin.

In another group of parent insulin analogues, the amino acid residue at position B1 has been deleted. A specific example from this group of parent insulin analogues is des(B1) human insulin.

In another group of parent insulin analogues, the amino acid residue at position B30 has been deleted. A specific example from this group of parent insulin analogues is des(B30) human insulin.

In another group of parent insulin analogues, the amino acid residue at position B28 is Asp. A specific example from this group of parent insulin analogues is Asp$^{B28}$ human insulin.

In another group of parent insulin analogues, the amino acid residue at position B28 is Lys and the amino acid residue at position B29 is Pro. A specific example from this group of parent insulin analogues is Lys$^{B28}$Pro$^{B29}$ human insulin.

In another group of parent insulin analogues the amino acid residue in position B30 is Lys and the amino acid residue in position B29 is any codable amino acid except Cys, Met, Arg and Lys. An example is an insulin analogue where the amino acid residue at position B29 is Thr and the amino acid residue at position B30 is Lys. A specific example from this group of parent insulin analogues is Thr$^{B29}$Lys$^{B30}$ human insulin.

In another group of parent insulin analogues, the amino acid residue at position B3 is Lys and the amino acid residue at position B29 is Glu. A specific example from this group of parent insulin analogues is Lys$^{B3}$Glu$^{B29}$ human insulin.

Examples of insulin derivatives according to the invention are the following compounds:

N$^{εB29}$—(N$^α$—(HOOC(CH$_2$)$_{14}$CO)-γ-Glu)   des(B30) human insulin;

N$^{εB29}$—(N$^α$—(HOOC(CH$_2$)$_{15}$CO)-γ-Glu)   des(B30) human insulin;

N$^{εB29}$—(N$^α$—(HOOC(CH$_2$)$_{16}$CO)-γ-Glu)   des(B30) human insulin;

N$^{εB29}$—(N$^α$—(HOOC(CH$_2$)$_{17}$CO)-γ-Glu)   des(B30) human insulin;

$N^{\epsilon B29}$—($N^\alpha$—(HOOC(CH$_2$)$_{18}$CO)-γ-Glu) des(B30) human insulin;

$N^{\epsilon B29}$—($N^\alpha$—(HOOC(CH$_2$)$_{16}$CO)-γ-Glu-N-(γ-Glu)) des(B30) human insulin;

$N^{\epsilon B29}$—($N^\alpha$—(Asp-OC(CH$_2$)$_{16}$CO)-γ-Glu) des(B30) human insulin;

$N^{\epsilon B29}$—($N^\alpha$—(Glu-OC(CH$_2$)$_{14}$CO)-γ-Glu) des(B30) human insulin;

$N^{\epsilon B29}$—($N^\alpha$—(Glu-OC(CH$_2$)$_{14}$CO—) des(B30) human insulin;

$N^{\epsilon B29}$—($N^\alpha$—(Asp-OC(CH$_2$)$_{16}$CO—) des(B30) human insulin;

$N^{\epsilon B29}$—($N^\alpha$—(HOOC(CH$_2$)$_{16}$CO)-α-Glu-N-(β-Asp)) des(B30) human insulin;

$N^{\epsilon B29}$—($N^\alpha$—(Gly-OC(CH$_2$)$_{13}$CO)-γ-Glu) des(B30) human insulin;

$N^{\epsilon B29}$—($N^\alpha$—(Sar-OC(CH$_2$)$_{13}$CO)-γ-Glu) des(B30) human insulin;

$N^{\epsilon B29}$—($N^\alpha$—(HOOC(CH$_2$)$_{13}$CO)-γ-Glu) des(B30) human insulin;

($N^{\epsilon B29}$—($N^\alpha$—(HOOC(CH$_2$)$_{13}$CO)-β-Asp) des(B30) human insulin;

$N^{\epsilon B29}$—($N^\alpha$—(HOOC(CH$_2$)$_{13}$CO)-α-Glu) des(B30) human insulin;

$N^{\epsilon B29}$—($N^\alpha$—(HOOC(CH$_2$)$_{16}$CO)-γ-D-Glu) des(B30) human insulin;

$N^{\epsilon B29}$—($N^\alpha$—(HOOC(CH$_2$)$_{14}$CO-β-D-Asp) des(B30) human insulin;

$N^{\epsilon B29}$—(N—HOOC(CH$_2$)$_{16}$CO-β-D-Asp) des(B30) human insulin;

$N^{\epsilon B29}$—(N—HOOC(CH$_2$)$_{14}$CO-IDA) des(B30) human insulin;

$N^{\epsilon B29}$—[N—(HOOC(CH$_2$)$_{16}$CO—N-(carboxyethyl)-Gly] des(B30) human insulin;

$N^{\epsilon B29}$—[N—(HOOC(CH$_2$)$_{14}$CO)—N-(carboxyethyl)-Gly] des(B30) human insulin; and $N^{\epsilon B29}$—[N—(HOOC(CH$_2$)$_{14}$CO)—N-(carboxymethyl)-β-Ala] des(B30) human insulin.

Insulin derivatives according to the invention may be provided in the form of essentially zinc free compounds or in the form of zinc complexes. When zinc complexes of an insulin derivative according to the invention are provided, two $Zn^{2+}$ ions, three $Zn^{2+}$ ions or four $Zn^{2+}$ ions can be bound to each insulin hexamer. Solutions of zinc complexes of the insulin derivatives will contain mixtures of such species.

In a further aspect of the invention, a pharmaceutical composition comprising a therapeutically effective amount of an insulin derivative according to the invention together with a pharmaceutically acceptable carrier can be provided for the treatment of type 1 diabetes, type 2 diabetes and other states that cause hyperglycemia in patients in need of such a treatment. An insulin derivative according to the invention can be used for the manufacture of a pharmaceutical composition for use in the treatment of type 1 diabetes, type 2 diabetes and other states that cause hyperglycaemia.

In a further aspect of the invention, there is provided a pharmaceutical composition for treating type 1 diabetes, type 2 diabetes and other states that cause hyperglycaemia in a patient in need of such a treatment, comprising a therapeutically effective amount of an insulin derivative according to the invention in mixture with an insulin or an insulin analogue which has a rapid onset of action, together with pharmaceutically acceptable carriers and additives.

In one embodiment the invention provides a pharmaceutical composition being a mixture of an insulin derivative according to the invention and a rapid acting insulin analogue selected group consisting of Asp$^{B28}$ human insulin; Lys$^{B28}$Pro$^{B29}$ human insulin and LyS$^{B3}$Glu$^{B29}$ human insulin.

In one embodiment the invention provides a pharmaceutical composition comprising $N^{\epsilon B29}$—$N^\alpha$—(HOOC(CH$_2$)$_{14}$CO)-γ-Glu) des(B30) human insulin and AspB28 human insulin together with pharmaceutically acceptable carriers and additives.

The insulin derivative according to the invention and the rapid acting insulin analogue can be mixed in a ratio from about 90/10%; about 70/30% or about 50/50%.

In a further aspect of the invention, there is provided a method of treating type 1 diabetes, type 2 diabetes and other states that cause hyperglycaemia in a patient in need of such a treatment, comprising administering to the patient a therapeutically effective amount of an insulin derivative according to the invention together with a pharmaceutically acceptable carrier and pharmaceutical acceptable additives.

In a further aspect of the invention, there is provided a method of treating type 1 diabetes, type 2 diabetes and other states that cause hyperglycaemia in a patient in need of such a treatment, comprising administering to the patient a therapeutically effective amount of an insulin derivative according to the invention in mixture with an insulin or an insulin analogue which has a rapid onset of action, together with a pharmaceutically acceptable carrier and pharmaceutical acceptable additives.

In a further aspect, the present invention relates to insulin derivatives which have an overall hydrophobicity which is essentially similar to that of human insulin.

In further aspect, the present invention relates to insulin derivatives which have a hydrophobic index, $k'_{rel}$, which is in the range of from about 2 to about 200.

In a further aspect, the insulin derivatives of the present invention have a hydrophobic index, $k'_{rel}$, which is in the range from about 0.02 to about 10, from about 0.1 to about 5; from about 0.5 to about 5; or from about 0.5 to about 2.

According to one embodiment of the present invention the insulin derivatives will comprise a side chain -W-X—Y-Z as defined above which has at least one hydrophilic and at least one hydrophobic region.

According to another embodiment of the present invention, the insulin derivatives will comprise a side chain -W-X—Y-Z as defined above which has at least one free carboxylic acid group and according to a further embodiment, the side chain will have at least two free carboxylic acid groups.

In another embodiment, the invention relates to a pharmaceutical composition comprising an insulin derivative according to the invention which is soluble at physiological pH values.

In another embodiment, the invention relates to a pharmaceutical composition comprising an insulin derivative according to the invention which is soluble at pH values in the interval from about 6.5 to about 8.5.

In another embodiment, the invention relates to a pharmaceutical composition with a prolonged profile of action which comprises an insulin derivative according to the invention.

In another embodiment, the invention relates to a pharmaceutical composition which is a solution containing from about 120 nmol/ml to about 2400 nmol/ml, from about 400 nmol/ml to about 2400 nmol/ml, from about 400 nmol/ml to about 1200 nmol/ml, from about 600 nmol/ml to about 2400 nmol/ml, or from about 600 nmol/ml to about 1200 nmol/ml of an insulin derivative according to the invention or of a mixture of the insulin derivative according to the invention with a rapid acting insulin analogue.

Hydrophobicity Data on Insulin Derivatives According to the Invention.

The hydrophobicity (hydrophobic index) of the insulin derivatives of the invention relative to human insulin, $k'_{rel}$, was measured on a LiChrosorb RP18 (5 μm, 250×4 mm) HPLC column by isocratic elution at 40° C. using mixtures of A) 0.1 M sodium phosphate buffer, pH 7.3, containing 10% acetonitrile, and B) 50% acetonitrile in water as eluents. The elution was monitored by following the UV absorption of the eluate at 214 nm. Void time, $t_0$, was found by injecting 0.1 mM sodium nitrate. Retention time for human insulin, $t_{human}$, was adjusted to at least $2t_0$ by varying the ratio between the A and B solutions. $k'_{rel}=(t_{derivative}-t_0)/(t_{human}-t_0)$. $k'_{rel}$ found for a number of insulin derivatives according to the invention are given in Table 1.

In a further embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention the formulation further comprises a pharmaceutically acceptable preservative which may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol,

TABLE 1

| Insulin derivative | $k'_{rel}$ |
|---|---|
| $N^{\epsilon B29}$—(N—HOOC(CH$_2$)$_{14}$CO-γ-Glu) des(B30) human insulin | 0.87 |
| $N^{\epsilon B29}$—(N—HOOC(CH$_2$)$_{16}$CO-γ-Glu) des(B30) human insulin | 1.15 |
| $N^{\epsilon B29}$—(N—HOOC(CH$_2$)$_{8}$CO-γ-Glu) des(B30) human insulin | 0.45 |
| $N^{\epsilon B29}$—(N—HOOC(CH$_2$)$_{16}$CO-γ-Glu-N-(γ-Glu) des(B30) human insulin | 1.17 |
| $N^{\epsilon B29}$—(N-(Asp-OC(CH$_2$)$_{16}$CO)-γ-Glu) des(B30) human insulin | 0.70 |
| $N^{\epsilon B29}$—(N-(Glu-OC(CH$_2$)$_{14}$CO-γ-Glu) des(B30) human insulin | 0.33 |
| $N^{\epsilon B29}$—(N-(Glu-OC(CH$_2$)$_{14}$CO-) des(B30) human insulin | 1.17 |
| $N^{\epsilon B29}$—(N—HOOC(CH$_2$)$_{16}$CO-α-Glu)-N-(β-Asp) des(B30) human insulin | 1.11 |
| $N^{\epsilon B29}$—(N-(Gly-OC(CH$_2$)$_{13}$CO-γ-Glu) des(B30) human insulin | 0.58 |
| $N^{\epsilon B29}$—(N-(Sar-OC(CH$_2$)$_{13}$CO-γ-Glu) des(B30) human insulin | 0.63 |
| $N^{\epsilon B29}$—(N—HOOC(CH$_2$)$_{16}$CO-α-Glu)-N-(AspAsp) des(B30) human insulin | 1.07 |
| $N^{\epsilon B29}$—(N-(Gly-OC(CH$_2$)$_{14}$CO-γ-Glu) des(B30) human insulin | 0.88 |
| $N^{\epsilon B29}$—(N—HOOC(CH$_2$)$_{15}$CO-γ-L-Glu) des(B30) human insulin | 1.13 |
| $N^{\epsilon B29}$—(N—HOOC(CH$_2$)$_{14}$CO-β-L-Asp) des(B30) human insulin | 0.69 |
| $N^{\epsilon B29}$—(N—HOOC(CH$_2$)$_{13}$CO-β-L-Glu) des(B30) human insulin | 0.54 |
| $N^{\epsilon B29}$—(N—HOOC(CH$_2$)$_{13}$CO-β-L-Asp) des(B30) human insulin | 0.47 |
| $N^{\epsilon B29}$—(N—HOOC(CH$_2$)$_{16}$CO-δ-L-Aad) des(B30) human insulin | 0.84 |
| $N^{\epsilon B29}$—(N—HOOC(CH$_2$)$_{16}$CO-γ-D-Glu) des(B30) human insulin | 1.4 |
| $N^{\epsilon B29}$—(N—HOOC(CH$_2$)$_{15}$CO-β-L-Asp) des(B30) human insulin | 1.09 |
| $N^{\epsilon B29}$—(N—HOOC(CH$_2$)$_{16}$CO-α-L-Asp) des(B30) human insulin | 1.49 |
| $N^{\epsilon B29}$—(N—HOOC(CH$_2$)$_{16}$CO-α-L-Glu) des(B30) human insulin | 1.51 |
| $N^{\epsilon B29}$—(N—HOOC(CH$_2$)$_{14}$CO-ε-L-LysCO—) des(B30) human insulin | 0.90 |
| $N^{\epsilon B29}$—(N—HOOC(CH$_2$)$_{16}$CO-β-L-Asp) des(B30) human insulin | 1.54 |
| $N^{\epsilon B29}$—(N-(Gly-OC(CH$_2$)$_{16}$CO-γ-L-Glu) des(B30) human insulin | 1.57 |
| $N^{\epsilon B29}$—[N—(HOOC(CH$_2$)$_{16}$CO-N-(carboxymethyl)-β-Ala] des(B30) human insulin | 1.13 |
| $N^{\epsilon B29}$—[N$^\alpha$—(HOOC(CH$_2$)$_{11}$)NHCO(CH$_2$)$_3$CO)-γ-L-Glu] des(B30) human insulin | 0.42 |

Pharmaceutical Compositions

Pharmaceutical compositions containing an insulin derivative according to the present invention may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. Further options are to administer the insulin nasally or pulmonally, preferably in compositions, powders or liquids, specifically designed for the purpose.

Injectable compositions of the insulin derivatives of the invention can be prepared using the conventional techniques of the pharmaceutical industry which involve dissolving and mixing the ingredients as appropriate to give the desired end product. Thus, according to one procedure, an insulin derivative according to the invention is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 19$^{th}$ edition, 1995.

In a further embodiment of the invention the formulation further comprises an isotonic agent which may be selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 19$^{th}$ edition, 1995.

Typical isotonic agents are sodium chloride, mannitol, dimethyl sulfone and glycerol and typical preservatives are phenol, m-cresol, methyl p-hydroxybenzoate and benzyl alcohol.

Examples of suitable buffers are sodium acetate, glycylglycine, HEPES (4-(2-hydroxyethyl)-1-piperazineethanesulfonic acid) and sodium phosphate.

A composition for nasal administration of an insulin derivative according to the present invention may, for example, be prepared as described in European Patent No. 272097 (to Novo Nordisk A/S).

Compositions containing insulins of this invention can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific insulin derivative employed, the age, body weight, physical activity, and diet of the patient, on a possible combination with other drugs, and on the severity of the state to be treated. It is recommended that the daily dosage of the insulin derivative of this invention be determined for each individual patient by those skilled in the art in a similar way as for known insulin compositions.

Where expedient, the insulin derivatives of this invention may be used in mixture with other types of insulin, e.g. insulin analogues with a more rapid onset of action. Examples of such insulin analogues are described e.g. in the European patent applications having the publication Nos. EP 214826 (Novo Nordisk A/S), EP 375437 (Novo Nordisk A/S) and EP 383472 (Eli Lilly & Co.).

The present invention is further illustrated by the following examples which, however, are not to be construed as limiting the scope of protection.

DEFINITIONS

By "insulin analogue" as used herein is meant a polypeptide which has a molecular structure which formally can be derived from the structure of a naturally occurring insulin, for example that of human insulin, by deleting and/or exchanging at least one amino acid residue occurring in the naturally occurring insulin and/or adding at least one amino acid residue. The added and/or exchanged amino acid residues can either be codable amino acid residues or other naturally occurring residues or purely synthetic amino acid residues The insulin analogues may be such wherein position 28 of the B chain may be modified from the natural Pro residue to one of Asp, Lys, or Ile. In another embodiment Lys at position B29 is modified to Pro. In one embodiment B30 may be Lys and then B29 can be any codable amino acid except Cys, Met, Arg and Lys.

Also, Asn at position A21 may be modified to Ala, Gln, Glu, Gly, His, Ile, Leu, Met, Ser, Thr, Trp, Tyr or Val, in particular to Gly, Ala, Ser, or Thr and preferably to Gly. Furthermore, Asn at position B3 may be modified to Lys or Asp. Further examples of insulin analogues are des(B30) human insulin; des(B30) human insulin analogues; insulin analogues wherein PheB1 has been deleted; insulin analogues wherein the A-chain and/or the B-chain have an N-terminal extension and insulin analogues wherein the A-chain and/or the B-chain have a C-terminal extension. Thus one or two Arg may be added to position B1.

By "insulin derivative" as used herein is meant a naturally occurring insulin or an insulin analogue which has been chemically modified, e.g. by introducing a side chain in one or more positions of the insulin backbone or by oxidizing or reducing groups of the amino acid residues in the insulin or by converting a free carboxylic group to an ester group or acylating a free amino group or a hydroxy group.

The expression "a codable amino acid" or "a codable amino acid residue" is used to indicate an amino acid or amino acid residue which can be coded for by a triplet ("codon") of nucleotides.

hGlu is homoglutamic acid.

α-Asp is the L-form of —HNCH(CO—)CH$_2$COOH.

β-Asp is the L-form of —HNCH(COOH)CH$_2$CO—.

α-Glu is the L-form of —HNCH(CO—)CH$_2$CH$_2$COOH.

γ-Glu is the L-form of —HNCH(COOH)CH$_2$CH$_2$CO—.

α-hGlu is the L-form of —HNCH(CO—)CH$_2$CH$_2$CH$_2$COOH.

δ-hGlu is the L-form of —HNCH(COOH)CH$_2$CH$_2$CH$_2$CO—.

β-Ala is —NH—CH$_2$—CH$_2$—COOH.

Sar is sarcosine (N-methylglycine).

The expression "an amino acid residue having a carboxylic acid group in the side chain" designates amino acid residues like Asp, Glu and hGlu. The amino acids can be in either the L- or D-configuration. If nothing is specified it is understood that the amino acid residue is in the L configuration.

The expression "an amino acid residue having a neutral side chain" designates amino acid residues like Gly, Ala, Val, Leu, Ile, Phe, Pro, Ser, Thr, Cys, Met, Tyr, Asn and Gln.

When an insulin derivative according to the invention is stated to be "soluble at physiological pH values" it means that the insulin derivative can be used for preparing injectable insulin compositions that are fully dissolved at physiological pH values. Such favourable solubility may either be due to the inherent properties of the insulin derivative alone or a result of a favourable interaction between the insulin derivative and one or more ingredients contained in the vehicle.

The following abbreviations have been used in the specification and examples:

| Aad: | Alpha-amino-adipic acid (homoglutamic acid) |
|---|---|
| Bzl = Bn: | benzyl |
| DIEA: | N,N-diisopropylethylamine |
| DMF: | N,N-dimethylformamide |
| IDA: | Iminodiacetic acid |
| Sar: | Sarcosine (N-methyl-glycine) |
| tBu: | tert-butyl |
| TSTU: | O-(N-succinimidyl)-1,1,3,3-tetramethyluronium tetrafluoroborate |
| THF: | Tetrahydrofuran |
| EtOAc: | Ethyl acetate |
| DIPEA: | Diisopropylethylamine |
| HOAt: | 1-Hydroxy-7-azabenzotriazole |
| TEA: | triethyl amine |
| Su: | succinimidyl = 2,5-dioxo-pyrrolidin-1-yl |
| TFA: | trifluoracetic acid |
| DCM: | dichloromethane |
| DMSO: | dimethyl sulphoxide |
| TLC: | Thin Layer Chromatography |
| RT: | room temperature |

EXAMPLES

Example 1

Synthesis of $N^{\epsilon B29}$—$N^{\alpha}$—$(HOOC(CH_2)_{14}CO)$-γ-Glu) des(B30) Human Insulin 200 mg of des(B30) human insulin was dissolved in 10 ml of 50 mM Na2CO3 (pH 10.2) contained in a tube which was placed in a water bath at 15° C. Methyl hexadecandioyl-Glu (OSu)-OMe (37.90 mg, prepared as described below), was dissolved in 10 ml of acetonitrile and subsequently added to the insulin solution. The reaction was stopped after 30 min by addition of 3.8 ml of 0.2 M ethanolamine adjusted to pH 9.0 with dilute HCl. The yield of the reaction was 37% as determined by RP-HPLC. The product precipitated after addition of 2.5 volumes of water and adjustment of pH to 5.5. The precipitate was then dissolved in 10 ml of water at pH 8 and placed in ice. To this solution was added 10 ml of ice cold 0.2 M NaOH for saponification and the mixture was incubated for 40 min with ice cooling and then adjusted to pH 5.5 to precipitate the product. The precipitate was isolated and dissolved in 5 ml of A-buffer (see below) and diluted with 33 ml of 42.5% w/w aqueous ethanol divided in three and subjected to anion exchange chromatography employing a Resource™ 6 ml anion exchange column eluted with a buffer system consisting of A-buffer: Tris 0.24% w/w, NH4Ac 0.25%, 42% ethanol w/w, pH 7.5 and B-buffer: Tris 0.24% w/w, NH4Ac 1.25%, 42% ethanol w/w pH 7.5. The sample was eluted by a flow of 6 ml/min in a gradient from 0 to 100% of B-buffer in 30 min. The fractions containing the desired compound were identified by RP-HPLC. The yield of the desired product was 15.3 mg (purity: 72.9%). The volume of the pooled fractions containing the desired compound was reduced to 20 ml under vacuum and this solution was then subjected to purification by RP-HPLC employing a reversed phase HPLC column Nucleosil, C4 250/10 mm, 10 μm, 300 Å. The buffer system consisted of A-buffer: 10 mM Tris, 15 mM (NH4)2SO4, 10% ethanol, pH 7.3 and B-buffer: 70% vol/vol ethanol.

The product was eluted with a gradient of from 10% to 60% of B-buffer in 120 min at a flow of 2 ml/min. The appropriate fractions were pooled and the compound was precipitated and lyophilized. The yield was 7.7 mg (purity: 99.4%).

Molecular weight, found by mass spectroscopy: 6097.2, calculated 6104.1. B-terminal peptide containing the side chain was obtained after digestion with *staphylococcus aureus* protease. Molecular weight, found by mass spectroscopy: 1413.1, calculated: 1413.5.

Preparation of Methyl hexadecandioyl-Glu(OSu)-OMe

Dimethyl hexadecandioate was saponified in MeOH using 1.0 equivalent of NaOH, and the mono-methyl ester was isolated upon HCl acidification by recrystallisation from heptane.

Mono-methyl hexadecandioate (275 mg, 0.91 mmol) was dissolved in THF (3 ml) and treated with succinimidyl tetramethyluroniumtetrafluoroborate (331 mg, 1.1 mmol) and N,N-diisopropylethylamine (188 μL, 1.1 mmol), and the mixture was stirred for 20 hours. The solvent was removed in vacuo, and the residue was dissolved in ethyl acetate and washed with 0.1 M HCl (twice) and water. The organic phase was dried over MgSO4, filtered and evaporated in vacuo to give 350 mg (96%) of methyl succinimidyl hexadecandioate.

1H-NMR (CDCl3) □: 3.66 (s, 3H), 2.83 (s, 4H), 2.60 (t, 2H), 2.30 (t, 2H), 1.74 (p, 2H), 1.62 (p, 2H), 1.40 (m, 2H), 1.35-1.22 (m, 18H).

Methyl succinimidyl hexadecandioate (240 mg, 0.58 mmol) in dimethylformamide (5 ml) was treated with Glu-OMe (93 mg, 0.58 mmol) and N,N-diisopropylethylamine (200 μL, 1.16 mmol). The mixture was stirred for 20 hours and then evaporated in vacuo. The residue was redissolved in ethyl acetate. Washing with 0.1 M HCl and water, followed by drying (MgSO4) and evaporation in vacuo, gave 226 mg (88%) of methyl hexadecandioyl-Glu-OMe.

1H-NMR □: 6.22 (d, 1H), 4.65 (m, 1H), 3.76 (s, 3H), 3.66 (s, 3H), 2.42 (t, 2H), 2.29 (m, 4H), 2.22 (t, 2H), 1.97 (m, 2H), 1.62 (m, 4H), 1.35-1.22 (m, 20H).

Methyl hexadecandioyl-Glu-OMe (200 mg, 0.45 mmol) was dissolved in dichloromethane (4 ml), cooled with an ice-bath and treated with dicyclohexylcarbodiimide (93 mg, 0.45 mmol) and N-hydroxysuccinimide (52 mg, 0.45 mmol). The mixture was stirred for 20 hours, filtered and evaporated in vacuo, to give 243 mg (100%) of the desired intermediate.

1H-NMR (CDCl3) □: 6.34 (d, 1H), 4.67 (m, 1H), 3.73 (s, 3H), 3.64 (s, 3H), 2.81 (s, 4H), 2.66 (m, 2H), 2.27 (m, 4H), 2.20 (t, 2H), 1.89 (m, 1H), 1.70 (m, 1H), 1.58 (m, 4H), 1.29-1.20 (m, 20H).

Example 2

Synthesis of NεB29-(Nα-(HOOC(CH2)16CO)-γ-Glu) des(B30) Human Insulin 300 mg of des(B30) human insulin was acylated, purified and isolated as described in Example 1, except that in the present example methyl octadecandioyl-Glu(OSu)-OMe (prepared as described below) was used as acylating agent instead of the methyl hexadecandioyl-Glu(OSu)-OMe used in Example 1. 25.5 mg of the title compound was obtained (purity: 97.4%). Molecular weight, found by mass spectroscopy: 6136.6, calculated: 6132. B-terminal peptide containing the ligand was obtained after digestion by *staphylococcus* aureus protease. Molecular weight, found by mass spectroscopy: 1439.1, Calculated: 1442.5.

Preparation of Methyl octadecandioyl-Glu(OSu)-OMe

This compound was prepared from dimethyl octadecandioate in analogy with the hexadecandioyl derivative described in Example 1.

1H-NMR (CDCl3) □: 6.20 (d, 1H), 4.70 (m, 1H), 3.78 (s, 3H), 3.67 (s, 3H), 2.84 (s, 4H), 2.70 (m, 2H), 2.30 (m, 4H), 2.22 (t, 2H), 1.93 (m, 1H), 1.70 (m, 1H), 1.62 (m, 4H), 1.33-1.23 (m, 24H).

Example 3

Synthesis of $N^{\epsilon B29}$—$N^{\alpha}$—(HOOC(CH$_2$)$_{16}$CO)-γ-Glu-N-(γ-Glu)) des(B30) Human Insulin In a similar way as described in Example 1, 300 mg of des(B30) human insulin was acylated with methyl octadecandioyl-Glu(Glu(OSu)-OMe)-OMe. Purification by anion exchange was performed as described above. However, prolonged elution with 100% B-buffer was conducted in order to elute the desired product. The fractions containing the desired product were identified by RP-HPLC and 47.5 mg was obtained at a purity of 55%. The volume of the fractions containing the desired product was reduced in vacuo and the resulting solution was subjected to purification by RP-HPLC employing a reversed phase HPLC Jupiter column, C4 250/10 mm, 10 μm, 300 Å from Phenomerex. The buffer system consisted of A-buffer: 0.1% TFA, 10% vol/vol ethanol and B-buffer: 80% vol/vol ethanol. The sample was eluted by a gradient from 40% to 60% B-buffer at 40° C. for 120 min at a flow of 2 ml/min. The appropriate fractions were pooled and lyophilized and 31.1 mg of the title compound was obtained (purity: 94%).

Molecular weight of the title compound found by mass spectroscopy: 6259.65, calculated: 6261.2. The molecular weight (by mass spectroscopy) of the B-terminal peptide containing the side chain, obtained after digestion with *staphylococcus aureus* protease was found to be 1569.88, calculated: 1569.88.

Preparation of Methyl octadecandioyl-Glu(Glu(OSu)-OMe)-OMe

Methyl octadecandioyl-Glu(OSu)-OMe (prepared as described in Example 2, 200 mg, 0.35 mmol) in dimethylformamide (5 ml) was treated with GluOMe (62 mg, 0.39 mmol) and N,N-diisopropylethylamine (90 μL, 53 mmol), and the mixture was stirred for 20 hours. The solvent was removed in vacuo, and the residue was dissolved in ethyl acetate and washed twice with 0.2 M HCl, water and brine. Drying over MgSO$_4$ and evaporation gave methyl octadecandioyl-Glu(Glu-OMe)-OMe, 180 mg (83%).

Methyl octadecandioyl-Glu(Glu-OMe)-OMe (180 mg, 0.29 mmol) was dissolved in THF (9 ml) and treated with succinimidyl tetramethyluroniumtetrafluoroborate (106 mg, 0.35 mmol) and N,N-diisopropylethylamine (60 μL, 0.35 mmol). The mixture was stirred overnight, evaporated, redissolved in ethyl acetate, and washed with 2×0.1 M HCl and water. Drying over MgSO$_4$ and evaporation gave 190 mg (93%) of the desired intermediate.

$^1$H-NMR (CDCl$_3$) δ: 6.73 (d, 1H), 6.43 (d, 1H), 4.69 (m, 1H), 4.56 (m, 1H), 3.77 (s, 3H), 3.74 (s, 3H), 3.66 (s, 3H), 2.85 (s, 4H), 2.72 (m, 2H), 2.41-2.12 (m, 8H), 2.95 (m, 2H), 1.72-1.56 (m, 6H), 1.35-1.22 (m, 22H).

Example 4

Synthesis of $N^{\epsilon B29}$—$N^{\alpha}$—(HOOC(CH$_2$)$_{14}$CO)-γ-L-Glu) des(B30) Human Insulin Des(B30) human insulin (500 mg, 0.088 mmol) was dissolved in 100 mM Na$_2$CO$_3$ (5 ml, pH 10.2) at room temperature. Tert-butyl hexadecandioyl-Glu(OSu)-OtBu (66 mg, 0.105 mmol, prepared as described below), was dissolved in acetonitrile (5 ml) and subsequently added to the insulin solution. After 30 mins, 0.2 M methylamine (0.5 ml) was added. pH was adjusted by HCl to 5.5, and the isoelectric precipitate was collected by centrifugation and dried in vacuo to give 525 mg. The coupling yield was 78% (RP-HPLC, C4 column; Buffer A: 10% MeCN in 0.1% TFA-water, Buffer B: 80% MeCN in 0.1% TFA-water; gradient 20% to 90% B in 16 minutes). The protected product was dissolved in TFA (10 ml), left 30 mins, and evaporated in vacuo. The crude product was dissolved in water and lyophilized (610 mg). 0454 was purified by RP-HPLC on C4-column, buffer A: 20% EtOH+0.1% TFA, buffer B: 80% EtOH+0.1% TFA; gradient 15-60% B, followed by HPLC on C4-column, buffer A: 10 mM Tris+15 mM ammonium sulphate in 20% EtOH, pH 7.3, buffer B: 80% EtOH, gradient 15-60% B. The collected fractions were desalted on Sep-Pak with 70% acetonitrile+0.1% TFA, neutralized by addition of ammonia and freeze-dried. The unoptimized yield was 64 mg, 12%. The purity as evaluated by HPLC was 99.2%. LCMS 6102.9, $C_{274}H_{411}N_{65}O_{81}S_6$ requires 6104.1. B-terminal peptide containing the side chain (RGFFYTPK($N^{\epsilon}$—($N^{\alpha}$—(HOOC(CH$_2$)$_{14}$CO)-γ-L-Glu) was obtained after digestion with *staphylococcus aureus* protease. MALDI-MS: 1413.1, calculated: 1412.7.

Preparation of tert-butyl hexadecandioyl-L-Glu(OSu)-OtBu

Hexadecadioic acid (40.0 g, 140 mmol) was suspended in toluene (250 ml) and the mixture was heated to reflux. N,N-dimethylformamide di-tert-butyl acetal (76.3 g, 375 mmol) was added drop-wise over 4 hours. The mixture was refluxed overnight. The solvent was removed in vacuo at 50° C., and the crude material was suspended in DCM/AcOEt (500 ml, 1:1) and stirred for 15 mins. The solids were collected by filtration and triturated with DCM (200 ml). The filtrated were evaporated in vacuo to give crude mono-tert-butyl hexadecandioate, 30 grams. This material was suspended in DCM (50 ml), cooled with ice for 10 mins, and filtered. The solvent was removed in vacuo to leave 25 gram crude mono-tert-butyl hexadecandioate, which was recrystallized from heptane (200 ml) to give mono-tert-butyl hexadecandioate, 15.9 g (33%). Alternatively to recrystallization, the mono-ester can be purified by silica chromatography in AcOEt/heptane.

$^1$H-NMR (CDCl$_3$) δ: 2.35 (t, 2H), 2.20 (t, 2H), 1.65-1.55 (m, 4H), 1.44 (s, 9H), 1.34-1.20 (m, 20H).

The mono tert-butyl ester (2 g, 5.8 mmol) was dissolved in THF (20 ml) and treated with TSTU (2.1 g, 7.0 mmol) and DIEA (1.2 ml, 7.0 mmol) and stirred overnight. The mixture was filtered, and the filtrate was evaporated in vacuo. The residue was dissolved in AcOEt and washed twice with cold 0.1 M HCl and water. Drying over MgSO$_4$ and evaporation in vacuo gave succinimidyl tert-butyl hexadecandioate, 2.02 g (79%).

$^1$H-NMR (CDCl$_3$) δ: 2.84 (s, 4H), 2.60 (t, 2H), 2.20 (t, 2H), 1.74 (p, 2H), 1.56 (m, 2H), 1.44 (s, 9H), 1.40 (m, 2H), 1.30-1.20 (m, 18H).

Succinimidyl tert-butyl hexadecandioate (1 g, 2.27 mmol) was dissolved DMF (15 ml) and treated with L-Glu-OtBu (0.51 g, 2.5 mmol) and DIEA (0.58 ml, 3.41 mmol) and the mixture was stirred overnight. The solvent was evaporated in vacuo, and the crude product was dissolved in AcOEt, and washed twice with 0.2 M HCl, with water and brine. Drying over MgSO$_4$ and evaporation in vacuo gave tert-butyl hexadecandioyl-L-Glu-OtBu, 1.2 g (100%).

$^1$H-NMR (CDCl$_3$) δ: 6.25 (d, 1H), 4.53 (m, 1H), 2.42 (m, 2H), 2.21 (m, 4H), 1.92 (m, 1H), 1.58 (m, 4H), 1.47 (s, 9H), 1.43 (s, 9H), 1.43-1.22 (m, 18H).

Tert-butyl hexadecandioyl-L-Glu-OtBu (1.2 g, 2.27 mmol) was dissolved in THF (15 ml) and treated with TSTU (0.82 g, 2.72 mmol) and DIEA (0.47 ml, 2.72 mmol) and stirred overnight. The mixture was filtered, and the filtrate was evaporated in vacuo. The residue was dissolved in AcOEt and washed twice with cold 0.1 M HCl and water. Drying over MgSO$_4$ and evaporation in vacuo gave tert-butyl hexadecandioyl-L-Glu(OSu)-OtBu, 1.30 g (92%).

$^1$H-NMR (CDCl$_3$) δ: 6.17 (d, 1H), 4.60 (m, 1H), 2.84 (s, 4H), 2.72 (m, 1H), 2.64 (m, 1H), 2.32 (m, 1H), 2.20 (m, 4H), 2.08 (m, 1H), 1.6 (m, 4H), 1.47 (s, 9H), 1.43 (s, 9H), 1.33-1.21 (m, 20H).

Example 5

Synthesis of N$^{\epsilon B29}$—(N$^\alpha$—(HOOC(CH$_2$)$_{16}$CO)-γ-L-Glu) des(B30) Human Insulin DesB30 insulin (50 mg, 9 μmol) was dissolved in 0.1 M aqueous Na$_2$CO$_3$ (0.65 ml), pH 10.5. Octadecandioyl-L-Glu (OSu) (50.1 mg, 9.9 μmol, prepared as described below) was dissolved in acetonitrile (0.65 ml) and added to the insulin solution; pH was 10.3. After 30 mins, 0.2 M methylamine (50 μl) was added. pH was adjusted by HCl to 5.5, and the isoelectric precipitate was collected by centrifugation and dried in vacuo. HPLC showed the crude coupling yield to be 52% (not optimized); C4 column; Buffer A: 10% MeCN in 0.1% TFA-water, Buffer B: 80% MeCN in 0.1% TFA-water; gradient 20% to 90% B in 16 minutes). LCMS 6133.2, C$_{276}$H$_{415}$N$_{65}$O$_{81}$S$_6$ requires 6132.2.

Preparation of octadecandioyl-L-Glu(OSu)

Octadecanedioic acid (2.5 g, 8.0 mmol) was suspended in DCM (60 mL), treated with triethylamine (1.16 mL, 8.3 mmol) and ice-cooled. Benzylchloroformate (1.14 mL) was added drop-wise under nitrogen and the mixture was stirred for 10 min, when DMAP (0,097 g, 0.80 mmol) was added. After stirring for 20 min at 4° C. (TLC, 1:1 AcOEt:heptane), the reaction was evaporated to dryness. The crude material (3.9 g) was dissolved in DCM (60 ml), treated with silica (15 g) and evaporated. The silica was loaded on a silica column (175 g), and the product was eluted with AcOEt/heptane 1:7 to 1:1. Evaporation of the desired fractions gave mono-benzyl octadecandioate (1.15 g, 36%).

$^1$H-NMR (CDCl$_3$) δ: 7.35 (m, 5H), 5.11 (s, 2H), 2.35 (t, 4H), 1.63 (t, 4H), 1.30-1.22 (m, 24).

Mono-benzyl octadecandioate was dissolved in DMF (3.5 mL) and THF (7 mL) and cooled with ice bath. DIEA (0.103 mL) and TSTU were added and the mixture was stirred 1 h at ice bath and at RT overnight. The solvent was evaporated in vacuo and the residue was dissolved in AcOEt and washed twice with 0.2 N HCl, saturated NaHCO$_3$, dried, filtered and evaporated to dryness to give succinimidyl mono-benzyl octadecandioate (0.25 g, 100%).

$^1$H-NMR (CDCl$_3$) δ: 7.35 (m, 5H), 5.11 (s, 2H), 2.83 (s, 4H), 2.60 (t, 2H), 2.35 (t, 2H), 1.80-1.60 (m, 4H), 1.40-1.20 (m, 24).

Succinimidyl mono-benzyl octadecandioate-(95 mg, 0.19 mmol) was dissolved DMF (1.5 ml) and treated with L-Glu-OBzl (49 mg, 0.21 mmol) and DIEA (50 □l, 0.28 mmol) and the mixture was stirred overnight. The solvent was evaporated in vacuo, and the crude product was dissolved in AcOEt, and washed twice with 0.2M HCl, with water and brine. Drying over MgSO$_4$ and evaporation in vacuo gave BzlO-octadecandioyl-L-Glu-OBzl, 114 mg (97%).

$^1$H-NMR (CDCl$_3$) δ: 7.35 (m, 5H), 6.22 (d, 2H), 5.17 (s, 2H), 5.11 (s, 2H), 4.71 (m, 1H), 2.37 (m, 4H), 2.22 (m, 3H), 1.98 (m, 1H), 1.63 (m, 4H), 1.31-1.20 (m, 24H).

BzlO-octadecandioyl-L-Glu-OBzl (110 g, 0.18 mmol) was dissolved in THF (2 ml) and treated with TSTU (64 mg, 0.21 mmol) and DIEA (36 μl, 0.21 mmol) and stirred overnight. The mixture was filtered, and the filtrate was evaporated in vacuo. The residue was dissolved in AcOEt and washed twice with cold 0.1 M HCl and water. Drying over MgSO$_4$ and evaporation in vacuo gave BzlO-octadecandioyl-L-Glu (OSu)-OBzl, 119 g (94%).

$^1$H-NMR (CDCl$_3$) δ: 7.36 (m, 5H), 6.40 (d, 2H), 5.19 (s, 2H), 5.11 (s, 2H), 4.75 (m, 1H), 2.82 (s, 4H), 2.68 (m, 1H), 2.59 (m, 1H), 2.35 (t, 2H), 2.19 (t, 2H), 1.62 (m, 4H), 1.32-1.21 (m, 24H).

BzlO-octadecandioyl-L-Glu(OSu)-OBzl (59 mg, 0.082 mmol) was dissolved in acetone/0.1% TFA (1 ml). Pd/C was added (20 mg). The flask was evacuated and filled with N$_2$ several times, and a H$_2$ filled balloon was connected. The mixture was stirred at RT 3 h, and then filtered through celite. Precipitation from heptane and evaporation of residual solvents gave octadecandioyl-L-Glu(OSu) (27 mg, 61%).

$^1$H-NMR (CDCl$_3$) δ: 6.32 (d, 1H), 4.70 (m, 1H), 3.70 (m, 1H), 3.06 (m, 2H), 2.88 (s, 4H), 2.62 (m, 2H), 2.35 (m, 2H), 2.24 (m, 1H), 1.74 (m, 1H), 1.64 (m, 2H), 1.50-1.20 (m, 26H).

Example 6

Synthesis of N$^{\epsilon B29}$—(N-(L-Asp-OC(CH$_2$)$_{16}$CO)-γ-L-Glu) des(B30) Human Insulin This compound was prepared in analogy with example 4, via reaction of L-Asp(OtBu)-OtBu with succinimidyl octadecandioate followed by activation with TSTU, reaction with L-GluOtBu, activation with TSTU, coupling with Des(B30) human insulin and deprotection by TFA.

LCMS 6247.5, calculated 6247.3.

Example 7

Synthesis of N$^{\epsilon B29}$—N-(L-Glu-OC(CH$_2$)$_{14}$CO-γ-L-Glu) des(B30) Human Insulin This compound was prepared in analogy with example 4, via reaction of L-Glu(OtBu)-OtBu with succinimidyl hexadecandioate followed by activation with TSTU, reaction with L-GluOtBu, activation with TSTU, coupling with Des(B30) human insulin and deprotection by TFA. LCMS 6261.3, calculated 6261.3.

Example 8

Synthesis of $N^{\epsilon B29}$—N-(L-Glu-OC(CH$_2$)$_{14}$CO—) des(B30) Human Insulin This compound was prepared in analogy with example 4, via reaction of L-Glu(OtBu)-OtBu with succinimidyl hexadecandioate followed by activation with TSTU, coupling with Des(B30) human insulin and deprotection by TFA. LCMS 6130.8, calculated 6132.2.

Example 9

Synthesis of $N^{\epsilon B29}$—(N—HOOC(CH$_2$)$_{16}$CO-α-L-Glu)-N-(β-L-Asp) des(B30) Human Insulin This compound was prepared in analogy with example 4, via reaction of tert-butyl succinimidyl octadecandioate with L-Glu(OtBu) followed by activation with TSTU, reaction with L-AspOtBu, activation with TSTU, coupling with Des(B30) human insulin and deprotection by TFA. LCMS 6246.9, calculated 6247.3.

Example 10

Synthesis of $N^{\epsilon B29}$—(N—HOOC(CH$_2$)$_{15}$CO-γ-L-Glu) des(B30) Human Insulin This compound was prepared in analogy with example 4, via reaction of tert-butyl succinimidyl heptadecandioate (A. C. Cope, U. Axen, E. P. Burrows, J. Weinlich, J. Am. Chem Soc. 1966, 88, 4228) with L-GluOtBu followed by activation with TSTU, coupling with Des(B30) human insulin and deprotection by TFA. LCMS 6118.3, calculated 6118.1.

Example 11

Synthesis of $N^{\epsilon B29}$—(N-(Gly-OC(CH$_2$)$_{13}$CO-γ-L-Glu) des(B30) Human Insulin This compound was prepared in analogy with example 4, via reaction of L-GlyOtBu with succinimidyl pentadecandioate followed by activation with TSTU, reaction with L-GluOtBu, activation with TSTU, coupling with Des(B30) human insulin and deprotection by TFA. LCMS 6147.5, calculated 6147.1.

Example 12

Synthesis of $N^{\epsilon B29}$—(N-(L-Sar-OC(CH$_2$)$_{13}$CO-γ-L-Glu) des(B30) Human Insulin This compound was prepared in analogy with example 4, via reaction of L-Sar-OtBu with succinimidyl octadecandioate, followed by activation with TSTU, reaction with L-GluOtBu, activation with TSTU, coupling with Des(B30) human insulin and deprotection by TFA. LCMS 6161.0, calculated 6161.1.

Example 13

Synthesis of $N^{\epsilon B29}$—(N—HOOC(CH$_2$)$_{16}$CO-α-L-Asp)-N-(β-L-Asp) des(B30) Human Insulin This compound was prepared in analogy with example 4, via reaction of tert-butyl succinimidyl octadecandioate with L-Asp(OtBu) followed by activation with TSTU, reaction with L-AspOtBu, activation with TSTU, coupling with Des(B30) human insulin and deprotection by TFA. LCMS 6233.8, calculated 6233.2.

Example 14

Synthesis of $N^{\epsilon B29}$—(N-(Gly-OC(CH$_2$)$_{14}$CO-γ-L-Glu) des(B30) Human Insulin This compound was prepared in analogy with example 4, via reaction of L-GlyOtBu with succinimidyl hexadecandioate followed by activation with TSTU, reaction with L-GluOtBu, activation with TSTU, coupling with Des(B30) human insulin and deprotection by TFA. LCMS 6160.7, calculated 6161.1.

Example 15

Synthesis of $N^{\epsilon B29}$—(N—HOOC(CH$_2$)$_{14}$CO-β-L-Asp) des(B30) Human Insulin This compound was prepared in analogy with example 4, via reaction of tert-butyl succinimidyl hexadecandioate with L-AspOtBu followed by activation with TSTU, coupling with Des(B30) human insulin and deprotection by TFA. LCMS 6089.8, calculated 6089.8.

Example 16

Synthesis of $N^{\epsilon B29}$—(N—HOOC(CH$_2$)$_{16}$CO-β-L-Asp) des(B30) Human Insulin This compound was prepared in analogy with example 4, via reaction of tert-butyl succinimidyl octadecandioate with L-AspOtBu followed by activation with TSTU, coupling with Des(B30) human insulin and deprotection by TFA. LCMS 6117.8, calculated 6118.1.

Example 17

Synthesis of $N^{\epsilon B29}$—N-(Gly-OC(CH$_2$)$_{16}$CO-γ-L-Glu) des(B30) Human Insulin This compound was prepared in analogy with example 4, via reaction of L-GlyOtBu with succinimidyl octadecandioate followed by activation with TSTU, reaction with L-GluOtBu, activation with TSTU, coupling with Des(B30) human insulin and deprotection by TFA. LCMS 6189.2, calculated 6189.2.

Example 18

Synthesis of N B29—(N—(HOOC(CH$_2$)$_{14}$CO-ε-L-LysCO—) des(B30) Human Insulin

This compound was prepared in analogy with example 4, via reaction of tert-butyl succinimidyl hexadecandioate with L-Lys(Z)-OtBu, followed by hydrogenation over Pd/C and in-situ activation by 4-nitrophenyl chloroformate, coupling with Des(B30) human insulin and deprotection by TFA. LCMS 6189.2, calculated 6189.2.

Example 19

Synthesis of $N^{\epsilon B29}$—(N—HOOC(CH$_2$)$_{16}$CO-α-L-Glu) des(B30) Human Insulin This compound was prepared in analogy with example 4, via reaction of tert-butyl succinimidyl octadecandioate with L-Glu(OtBu) followed by activation with TSTU, coupling with Des(B30) human insulin and deprotection by TFA. LCMS 6132.1, calculated 6132.2.

Example 20

Synthesis of $N^{\epsilon B29}$—(N—HOOC(CH$_2$)$_{16}$CO-α-L-Asp) des(B30) Human Insulin This compound was prepared in analogy with example 4, via reaction of tert-butyl succinimidyl octadecandioate with L-Asp(OtBu) followed by activation with TSTU, coupling with Des(B30) human insulin and deprotection by TFA. LCMS 6117.8, calculated 6118.1.

Example 21

Synthesis of $N^{\epsilon B29}$—(N—HOOC(CH$_2$)$_{15}$CO-β-L-Asp) des(B30) Human Insulin This compound was prepared in analogy with example 4, via reaction of tert-butyl succinimidyl heptadecandioate with L-AspOtBu followed by activation with TSTU, coupling with Des(B30) human insulin and deprotection by TFA. LCMS 6104.2, calculated 6104.1.

Example 22

Synthesis of $N^{\epsilon B29}$—(N—HOOC(CH$_2$)$_{16}$CO-γ-D-Glu) des(B30) Human Insulin This compound was prepared in analogy with example 4, via reaction of tert-butyl succinimidyl octadecandioate with D-GluOtBu followed by activation with TSTU, coupling with Des(B30) human insulin and deprotection by TFA. LCMS 6132.4, calculated 6132.2.

Example 23

Synthesis of $N^{\epsilon B29}$—(N—HOOC(CH$_2$)$_{16}$CO-δ-L-Aad) des(B30) Human Insulin This compound was prepared in analogy with example 4, via reaction of tert-butyl succinimidyl octadecandioate with L-AadOtBu (prepared from commercial L-Aad(OMe) by tert-butylation with AcOtBu/BF$_3$.OEt$_2$ and saponification of the methyl ester), followed by activation with TSTU, coupling with Des(B30) human insulin and deprotection by TFA. LCMS 6116.9, calculated 6118.1.

Example 24

Synthesis of $N^{\epsilon B29}$—(N—HOOC(CH$_2$)$_{13}$CO-β-L-Asp) des(B30) Human Insulin This compound was prepared in analogy with example 4, via reaction of tert-butyl succinimidyl pentadecandioate with L-AspOtBu followed by activation with TSTU, coupling with Des(B30) human insulin and deprotection by TFA. LCMS 6074.7, calculated 6076.1.

Example 25

Synthesis of $N^{\epsilon B29}$—(N—HOOC(CH$_2$)$_{13}$CO-β-L-Glu) des(B30) Human Insulin This compound was prepared in analogy with example 4, via reaction of tert-butyl succinimidyl pentadecandioate with L-GluOtBu followed by activation with TSTU, coupling with Des(B30) human insulin and deprotection by TFA. MALDI-MS 6080.6, calculated 6076.1.

Example 26

Synthesis of $N^{\epsilon B29}$—(N—HOOC(CH$_2$)$_{14}$CO-β-D-Asp) des(B30) Human Insulin This compound was prepared in analogy with example 4, via reaction of tert-butyl succinimidyl hexadecandioate with D-AspOtBu followed by activation with TSTU, coupling with Des(B30) human insulin and deprotection by TFA. LCMS 6089.1, calculated 6090.1.

Example 27

Synthesis of $N^{\epsilon B29}$—(N—HOOC(CH$_2$)$_{16}$CO-β-D-Asp) des(B30) Human Insulin This compound was prepared in analogy with example 4, via reaction of tert-butyl succinimidyl octadecandioate with D-AspOtBu followed by activation with TSTU, coupling with Des(B30) human insulin and deprotection by TFA. LCMS 6117.1, calculated 6118.1.

Example 28

Synthesis of $N^{\epsilon B29}$—(N—HOOC(CH$_2$)$_{14}$CO-IDA) des(B30) Human Insulin This compound was prepared in analogy with example 4, via reaction of tert-butyl 3,4-dihydro-4-oxo-1,2,3-benzotriazin-3-yl hexadecandioate with iminodiacetic acid followed by activation with TSTU, coupling with Des(B30) human insulin and deprotection by TFA. LCMS 6089.1, calculated 6090.1.

Example 29

Synthesis of $N^{\epsilon B29}$—[N—(HOOC(CH$_2$)$_{16}$CO)—N-(carboxymethyl)-β-Ala] des(B30) Human Insulin A1N, B1N-diBoc DesB30 Human insulin (Kurtzhals P; Havelund S; Jonassen I; Kiehr B; Larsen U D; Ribel U; Markussen J Biochemical Journal, 1995, 312, 725-731) (186 mg, 0.031 mmol) was dissolved in DMSO (1.8 ml). A solution of tert-butyl octadecandioyl-N-(tert-butoxycarbonylmethyl)-β-Ala-OSu (27 mg, 0.04 mmol) in THF (1.8 ml) and triethylamine (0.045 ml, 0.31 mmol) was added (pH was 10). After slowly stirring at room temperature for 45 min the reaction was quenched with 0.2M methylamine in THF (0,20 ml). Water (5 ml) was added and pH was adjusted to 5.5 with 1 N HCl. The isoelectric precipitate was collected by centrifugation and freeze dried to give 150 mg. The coupling yield was 74% (LCMS m/z: 2148.9 [(M+3)/3], rt 5.04.) The protected product was dissolved in TFA (2.5 ml) and left for 1 h and evaporated in vacuo. The crude product was purified by RP-HPLC on C4-column, buffer A: 0.1% TFA, buffer B: MeCN+0.1% TFA; gradient 10-70% B. The collected fractions were freeze-dried. The yield was 75 mg, 52%. The purity as evaluated by HPLC was 97.2%.

MALDI-MS: 6132.1, calculated: 6132.2.

Preparation of tert-butyl octadecandioyl-N-(tert-butoxycarbonylmethyl)-β-Ala-OSu Octadecanedioic acid (5.64 g, 17.9 mmol) was dissolved in toluene (80 ml) at 115° C. N,N-dimethylformamide di-tert-butylacetal (12.9 ml, 53.8 mmol) was added drop-wise over 1.5 h. After refluxing for 3 h more N,N-dimethylformamide di-tert-butylacetal (2.15 ml) was added over 20 min. Reflux was continued over night and more N,N-dimethylformamide di-tert-butylacetal (2.15 ml) was added over 20 min. After stirring for another 2 h. the reaction mixture was cooled to RT. Water and DCM was added. The diacid can was removed by filtration. The filtrate was concentrated on silica gel (40 g) and purified on a 1.5 L silicagel column using DCM/MeOH 14:1. Octadecandioic acid mono-tert-butyl ester was isolated in 53% yield (3.52 g).

LC-MS: 393 (M+Na), rt 6.40.

$^1$H-NMR (DMSO-d$_6$): δ 1.22 (br s, 24H), 1.38 (s, 9H), 1.47 (m, 4H), 2.14 (t, 2H), 2.18 ppm (t, 2H).

To a solution of mono-tert-butyl octadecanedioate (1.00 g, 2.7 mmol) in dry THF (8 ml), was added DIPEA (0,555 ml, 3.2 mmol) followed by TSTU (1.00 g, 3.2 mmol). The reaction mixture was stirred under nitrogen for 18 h. The solvent had evaporated. AcOEt was added to the residue and the resulting suspension was filtered. The filtrate was washed with cold 0.1 M HCl (2×) and water, dried and concentrated to give succinimidyl tert-butyl octadecandioate as a white solid.

$^1$H-NMR (CDCl$_3$): δ 1.25 (m s, 20H), 1.39 (m, 2H) 1.44 (s, 9H), 1.58 (m, 4H), 1.74 (p, 2H), 2.2 (t, 2H), 2.60 (t, 2H), 2,85 ppm (m, 2H).

To a suspension of H-Gly-OtBu (1.00 g, 6.0 mmol) in dry DMF (6 ml) was added triethyl amine (0.835 ml, 6.0 mmol). A precipitation of triethyl amine hydrochloride was observed. A solution of benzyl acrylate (0.910 ml, 6.0 mmol) in DMF (6 ml) was added. The resulting suspension was stirred at room temperature for 2 days. The precipitate was removed by filtration and the filtrate was concentrated. The residue was dissolved in AcOEt and washed with sat. NaHCO$_3$. The organic layer was dried (MgSO$_4$), filtered and concentrated to give a clear oil, which was purified by flash chromatography using AcOEt/heptane 1:3 and 1:1 as eluent. N-tert-butoxycarbonylmethyl)-β-Ala-OBn was isolated in 29% yield (0.505 g).

$^1$H-NMR (CDCl$_3$) δ: ppm 1.43 (s, 9H), 2.55 (t, 2H), 2.92 (t, 2H), 3.30 (s, 2H), 5.15 (s, 2H), 7.65 (m, 5H).

Succinimidyl tert-butyl octadecandioate (0,15 g, 0.32 mmol) and N-(tert-butoxycarbonylmethyl)-β-Ala-OBn (0.10 g, 0,32 mmol) were dissolved in dry DMF (2.5 ml) and DIEA (0,070 ml, 0.38 mmol) was added. After stirring under nitrogen for 30 min HOAt (0,045 g, 0.32 mmol) was added and the mixture turned yellow. Stirring was continued at RT under nitrogen for convenience reasons for 13 days. The reaction mixture was concentrated. The residue dissolved in AcOEt, washed with 0.1N HCl (2×) and water, dried (Na$_2$SO$_4$) and concentrated to a give tert-butyl octadecandioyl-N-(tert-butoxycarbonylmethyl)-β-Ala-OBn as a white oil. 205 mg, Yield 99%.

$^1$H-NMR (CDCl$_3$) δ: ppm 1.25 (m, 26H), 1.45 (s, 9H), 1.50 (s, 9H), 1.6 (m, 4H), 2.20 (t, 2H), 2.40 (t, 2H), 2.75 (q, 2H), 3.62 (t, 2H), 3.97 (s, 2H), 5.20 (s, 2H); 7.35 (m, 5H).

Tert-butyl octadecandioyl-N-(tert-butoxycarbonylmethyl)-β-Ala-OBn (200 mg, 0.31 mmol) was dissolved in EtOAc (10 ml) and THF (5 ml). 10% Pd/C was added and the mixture was hydrogenated at 1 atm for 16 h. The reaction mixture was filtered and concentrated to give tert-butyl octadecandioyl-N-(tert-butoxycarbonylmethyl)-β-Ala-OH as a clear oil. Yield 180 mg, 100%.

$^1$H-NMR (CDCl$_3$) δ: ppm 1.25 (m, 26H), 1.45 (s, 9H), 1.50 (s, 9H), 1.6 (m, 4H), 2.20 (t, 2H), 2.40 (t, 2H), 2.70 (m, 2H), 3.65 (m, 2H), 4.05 (s, 2H).

Tert-butyl octadecandioyl-N-(tert-butoxycarbonylmethyl)-β-Ala-OH (0.110 g, 0.2 mmol) was dissolved in dry THF (2 ml). DIEA (0,045 ml, 0.24 mmol) and TSTU (0.075 g, 0.24 mmol) was added. The mixture was stirred under nitrogen for 18 h. The reaction mixture was filtered. AcOEt was added to the filtrate and washed with 0.2 M HCl (2×), brine (1×), dried (Na$_2$SO$_4$) and concentrated to give tert-butyl octadecandioyl-N-(tert-butoxycarbonylmethyl)-β-Ala-OSu as a clear syrup. Yield 124 mg, 96%.

$^1$H-NMR (CDCl$_3$) δ: ppm 1.25 (m, 26H), 1.40 (s, 9H), 1.57 (s, 9H), 1.6 (m, 4H), 2.40 (m, 4H), 2.58 (br s, 4H), 3.0 (t, 2H), 3.7 (t, 2H), 4.03 (s, 2H).

Example 30

Synthesis of N$^{εB29}$—[N—(HOOC(CH$_2$)$_{16}$CO)—N-(2-carboxyethyl)-Gly] des(B30) Human Insulin A1N, B1N-diBoc DesB30 Human insulin (Kurtzhals P; Havelund S; Jonassen I; Kiehr B; Larsen U D; Ribel U; Markussen J Biochemical Journal, 1995, 312, 725-731) (120 mg, 0.020 mmol) was dissolved in DMSO (1.2 ml). A solution of tert-butyl octadecandioyl-N-(2-(tert-butoxycarbonyl)ethyl)-Gly-OSu (16 mg, 0.025 mmol) in THF (1.2 ml) and triethylamine (0.033 ml, 0.24 mmol) was added (pH was 10). After slowly stirring at room temperature for 3 h and 20 min water (4 ml) was added and pH was adjusted to 5.5 with 1 N HCl. The isoelectric precipitate was collected by centrifugation, washed with water and isolated by centrifugation. The product was freeze dried. The crude product was purified by RP-HPLC on C18-column, buffer A: 0.1% TFA, buffer B: MeCN+0.1% TFA; gradient 20-90% B. The collected fractions were freeze-dried. The unoptimized coupling yield was 15 mg, 11% (MALDI-MS 6441, calculated: 6444.5) The protected product was dissolved in TFA (1 ml) and left for 1 h and evaporated in vacuo. The crude product was purified by RP-HPLC on C4-column, buffer A: 0.1% TFA, buffer B: MeCN+0.1% TFA; gradient 10-80% B, and by RP-HPLC on C4-column, buffer A: 20% EtOH+0.1% TFA, buffer B: 80% EtOH+0.1% TFA; gradient 15-60% B, followed by HPLC on C4-column, buffer A: 10 mM Tris+15 mM ammonium sulphate in 20% EtOH, pH 7.3, buffer B: 80% EtOH, gradient 15-60% B. The collected fractions were desalted on Sep-Pak with 70% acetonitrile+0.1% TFA, neutralized by addition of ammonia and freeze-dried. The unoptimized yield was 1.8 mg, 13%. The purity as evaluated by HPLC was 96.4%.

MALDI: 6132.1, calculated: 6132.2.

Preparation of tert-butyl octadecandioyl-N-(2-(tert-butoxycarbonyl)ethyl)-Gly-OSu H-Gly-OBn, HCl (3.03 g, 15 mmol) was dissolved in dry DMF (15 ml) and cooled on an ice bath. TEA (2.10, 15 mmol) was added under precipitation of TEA-hydrochloride. The suspension was stirred for 5 min before t-butyl acrylate (2.20 ml, 15 mmol) was added. The cooling bath was allowed to reach RT slowly and stirring was continued under nitrogen for 2 days. The reaction mixture was filtered and the filtrate was concentrated. The residue, still containing DMF, was dissolved in AcOEt and washed with sat aq NaHCO$_3$ (2×) and water (1×). The organic layer was filtered before drying (Na$_2$SO$_4$) and concentration to give a yellow oil. Purification by flash chromatography or preparative HPLC gave N-(2-(tertbutoxycarbonyl)ethyl)-Gly-OBn as a clear oil (0.739 g, 17%).

$^1$H-NMR (CDCl$_3$) δ: ppm 1.46 (s, 9H) 2.50-2.61 (m, 2H) 2.82-2.99 (m, 2H) 3.31 (s, 2H) 5.14 (s, 2H) 7.29-7.43 (m, 5H).

N-(2-(Tert-butoxycarbonyl)ethyl)-Gly-OBn (0.030 g, 0.1 mmol) and succinimidyl tertbutyloctadecanedioate (described in example 29, 0.050 mg, 0.1 mmol) was suspended in dry DMF (1 ml). HOAt (0.014 g, 0.1 mmol) and DIEA (0.21 ml, 1.2 mmol) was added. The yellow reaction mixture was stirred under nitrogen for 42 h. The reaction mixture was concentrated. The residue was redissolved in AcOEt and washed with 0.1 N HCl (2×), water (1×), dried (Na$_2$SO$_4$) and concentrated to give tert-butyl octadecandioyl-N-(2-(tert-butoxycarbonyl)ethyl)Gly-OBn in 85% yield (55 mg).

$^1$H-NMR (CDCl$_3$) δ: ppm 1.3 (m, 26H) 1.38 (s, 9H), 1.46 (s, 9H), 1.6 (m, 4H), 2.2 (m, 2H), 2.35 (m, 2H), 2.65 (m, 2H), 2.85 (s, 2H) 3.65 (m, 2H), 5.15 (s, 2H) 7.35 (m, 5H).

Tert-butyl octadecandioyl-N-(2-(tert-butoxycarbonyl) ethyl)-Gly-OBn (0.054 g, 0.08 mmol) was dissolved in THF (2 ml). 10% Palladium on charcoal was added and the mixture was hydrogenated at 1 atm and RT over the week-end. The dry reaction mixture was dissolved in AcOEt and filtered 3 times to remove the carbon. The filtrate was concentrated to give in tert-butyl octadecandioyl-N-(2-(tert-butoxycarbonyl)ethyl)-Gly-OH 80% yield (37 mg).

$^1$H-NMR (CDCl$_3$) δ: ppm 1.3 (m, 26H) 1.40 (s, 9H), 1.46 (s, 9H), 1.6 (m, 4H), 1.75 (p, 2H), 2.2 (m, 2H), 2.35 (m, 2H), 2.63 (m, 2H), 2.83 (s, 2H).

Tert-butyl octadecandioyl-N-(2-(tert-butoxycarbonyl) ethyl)-Gly-OH (0.07 mmol) was dissolved in dry THF (2 ml). TSTU (24 mg, 0.08 mmol) and DIPEA (15 uL, 0.08 mmol) was added. The mixture was stirred at RT under nitrogen. After 19 h the reaction had not finished according to TLC (DCM/MeOH 10:1). More DIEA was added (20 uL, 0.11 mmol) and stirring was continued. After 42 h the reaction mixture was filtered. The filtrate was diluted with AcOEt and washed with 0.1 N HCl (2×) and brine (1×), dried (Na$_2$SO$_4$) and concentrated to a give tert-butyl octadecandioyl-N-(2-(tert-butoxycarbonyl)ethyl)-Gly-OSu as a white solid in 84% yield (36 mg).

$^1$H-NMR (CDCl$_3$) δ: ppm 1.3 (m, 26H) 1.40 (m, 2H), 1.44 (s, 9H), 1.46 (s, 9H), 1.58 (m, 2H), 1.73 (p, 2H), 2.2 (t, 2H), 2.60 (t, 2H), 2.8 (m, 6H).

Example 31

Synthesis of N$^{εB29}$—[N—(HOOC(CH$_2$)$_{14}$CO)—N-(carboxyethyl)-Gly] des(B30) Human Insulin This compound was prepared in analogy with example 30, via reaction of N-(2-(tertbutoxycarbonyl)ethyl)-Gly-OBn with succinimidyl hexadecandioate (described in example 4) followed by debenzylation, activation with TSTU, coupling with A1N, B1N-diBOC-Des(B30) human insulin and deprotection by TFA.

MALDI-MS: 6093.0, calculated 6104.1.

Example 32

Synthesis of N$^{εB29}$—[N—(HOOC(CH$_2$)$_{14}$CO)—N-(carboxymethyl)-β-Ala] des(B30) Human Insulin This compound was prepared in analogy with example 29 via reaction of N-(tertbutoxycarbonylmethyl)-β-Ala-OBn with succinimidyl hexadecandioate (described in example 4) followed by debenzylation, activation with TSTU, coupling with A1N, B1N-diBOC-Des(B30) human insulin and deprotection by TFA.

MALDI-MS: 6097.6, calculated 6104.1.

Example 33

Synthesis of N$^{εB29}$—[N$^α$—(HOOC(CH$_2$)$_{11}$)NHCO (CH$_2$)$_3$CO)-γ-L-Glu] des(B30) Human Insulin This compound was prepared similarly as described in example 1 using (MeOOC(CH$_2$)$_{11}$)NHCO(CH$_2$)$_3$CO)-Glu (OSu)-OMe, prepared as described below, as acylating agent.

LCMS (electrospray): M+3: 2049, calculated 2050; M+4: 1538, calculated 1537.8; M+5: 1231, calculated 1230.4.

MALDI-TOF MS: Calculated: 6147; found: 6153.

Preparation of (MeOOC(CH$_2$)$_{11}$)NHCO(CH$_2$)$_3$CO)-Glu(OSu)-OMe

MeOH (40 ml) was cooled to 0-50° C., and SOCl$_2$ (4 ml) was added drop wise with stirring during 30 minutes. 12-Aminododecanoic acid (3 g, 13.9 mmol) was added and the resulting suspension was stirred at 0-5° C. while the ice in cooling bath melted and allowed to warm to room temperature during 16 hours. The mixture was filtered and the solid was dried by suction to afford 2.23 g (60%) of 12-aminododecanoic acid methyl ester hydrochloride. From the mother liquor a further batch of 0.92 g (25%) was isolated.

$^1$H-NMR (DMSO-d$_6$) δ: 7.97 (bs, 3H), 3.58 (s, 3H), 2.73 (m, 2H, 2.28 (t, 2H), 1.52 (m, 4H), 1.25 ("s", 14H).

The 12-aminododecanoic acid methyl ester hydrochloride (1 g, 3.8 mmol) was suspended in THF (15 ml) and added glutaric acid anhydride (1.29 g, 3.8 mmol) and TEA (0.52 ml, 3.8 mmol) and the resulting mixture (suspension) was stirred at room temperature for 16 hours. Water (75 ml) was added gradually. After 25 ml, a solution was obtained and later a suspension appeared. The mixture was stirred at room temperature for 1 hour and filtered. The solid was washed with water and dried in vacuo. This afforded 1.02 g (80%) of 12-(4-carboxybutyrylamino)dodecanoic acid methyl ester.

$^1$H-NMR (DMSO-d$_6$) δ:12 (bs, 1H), 7.73 (t, 1H), 3.57 (s, 3H), 3.00 (q, 2H), 2.28 (t, 2H), 2.18 (t, 2H), 2.06 (t, 2H), 1.69 (p, 2H), 1.50 (p, 2H), 1.36 (p, 2H), 1.23 ("s", 14H).

The 12-(4-carboxybutyrylamino)dodecanoic acid methyl ester (0.33 g, 0.95 mmol) was dissolved in a mixture of THF and DMF (2:1, 6 ml), and added DIEA (0.178 ml, 1.04 mmol). The mixture was cooled to 0-5° C. and TSTU (0.314 g, 1.04 mmol) was added. The mixture was stirred at 0-5° C. for 1 hour and at room temperature for 16 hours. The mixture was concentrated to dryness in vacuo. The residue (OSu-activated 12-(4-carboxybutyrylamino)dodecanoic acid methyl ester) was dissolved in DMF (10 ml) and added DIEA (0.24 ml, 1.4 mmol) and H-Glu-OMe (0.168 g, 1.04 mmol) and the mixture was stirred at room temperature for 16 hours. The mixture was concentrated in vacuo and the residue was dissolved in AcOEt (100 ml) and washed with 0.2M hydrochloric acid (3×50 ml). The organic phase was dried (Na$_2$SO$_4$) and concentrated in vacuo. This afforded 0.358 g (78%) of (MeOOC(CH$_2$)$_{11}$)NHCO(CH$_2$)$_3$CO)-Glu-OMe.

$^1$H-NMR (DMSO-d$_6$), δ: 12 (bs, 1H), 8.22 (d, 1H), 7.73 (t, 1H), 4.24 (m, 1H), 3.61 (s, 3H), 3.57 (s, 3H), 3.00 (q, 2H), 2.27 (m, 4H), 2.10 (t, 2H), 2.04 (t, 2H), 1.9 (m, 1H), 1.8 (m, 1H), 1.68 (t, 2H), 1.50 (m, 2H), 1.36 (m, 2H), 1.23 ("s", 14H).

(MeOOC(CH$_2$)$_{11}$)NHCO(CH$_2$)$_3$CO)-Glu-OMe (0.36 g, 0.36 mmol) was dissolved in THF (10 ml) and cooled to 0-5°

C. DIEA (0.13 ml) and TSTU (0.129 g, 0.43 mmol) were added and the mixture was stirred at 0-5° C. for some hours and at room temperature for 3 days. The mixture was concentrated in vacuo. The residue was dissolved in AcOEt (100 ml) and washed with 0.2N hydrochloric acid (3×50 ml) and saturated aqueous NaHCO$_3$ (3×100 ml). Drying (Na$_2$SO$_4$) and concentration in vacuo afforded 0.17 g (84%) of (MeOOC(CH$_2$)$_{11}$)NHCO(CH$_2$)$_3$CO)-Glu(OSu)-OMe.

$^1$H-NMR (DMSO-d$_6$), selected peaks, δ: 8.27 (d, 1H), 7.72 (t, 1H), 4.31 (m, 1H), 3.63 (s, 3H), 3.57 (s, 3H), 3.00 (q, 2H), 2.81 (s, 4H), 2.28 (t, 2H), 2.12 (t, 2H), 2.05 (t, 2H), 1.70 (m, 2H), 1.50 (m, 2H), 1.35 (m, 2H), 1.23 ("s", 14H).

Example 34

Synthesis of N$^{εB29}$—[N$^α$—(HOOC(CH$_2$)$_{11}$)NHCO(CH$_2$)$_2$CO)-γ-L-Glu] des(B30) Human Insulin This compound was prepared similarly as described in example 1 using (MeOOC(CH$_2$)$_{11}$)NHCO(CH$_2$)$_2$CO)-Glu(OSu)-OMe, which in turn was prepared similarly as described in example 33 using succinic acid anhydride instead of glutaric acid anhydride, as acylating agent.

MALDI-TOF MS: Calculated: 6133; found: 6134.

Example 35

Synthesis of N$^{εB29}$—[N$^α$—(HOOC(CH$_2$)$_{16}$CO)]-Gly-γ-L-Glu des(B30) Human Insulin This compound was prepared similarly as described in example 4 using tert-butyl octadecandioyl-Gly-Glu(OSu)-OtBu, prepared as described below as acylating agent.

MALDI-TOF MS: Calculated: 6189; found: 6191.

Preparation of tert-butyl octadecandioyl-Gly-Glu(OSu)-OtBu

Z-Gly-OH (1.0 g, 4.78 mmol) was added THF (10 ml), DIEA (0.98 ml, 5.74 mmol), and TSTU (1.7 g, 5.74 mmol) and the resulting mixture was stirred at room temperature for 2 hours. AcOEt (100 ml) was added and the mixture was washed with 0.2N hydrochloric acid (100 ml) and water (2×100 ml). The organic phase was dried (Na$_2$SO$_4$) and concentrated in vacuo to afford 1.34 g (92%) of Z-Gly-OSu as an oil.

$^1$H-NMR (CDCl$_3$), δ: 7.35 (s, 5H), 5.32 (t, 1H), 5.15 (s, 2H), 4.35 (d, 2H), 2.83 (s, 4H).

Z-Gly-OSu (1.3 g, 4.25 mmol) was dissolved in DMF (15 ml) and DIEA (1.82 ml, 10.6 mmol) and H-Glu-O$^t$Bu (0.949 g, 4.67 mmol) were added and the resulting mixture was stirred at room temperature for 16 hours. AcOEt (100 ml) was added and the mixture was washed with 0.2N hydrochloric acid (100 ml) and water (2×100 ml). The organic phase was dried (Na$_2$SO$_4$) and concentrated in vacuo to afford 1.7 g (quant.) of Z-Gly-Glu-O$^t$Bu as an oil.

$^1$H-NMR (CDCl$_3$), δ: 7.33 (s, 5H), 7.1 (d, 1H), 5.80 (t, 1H), 5.12 (s, 2H), 4.53 (m, 1H), 3.90 (d, 2H), 2.36 (t, 2H), 2.22 (m, 1H), 1.95 (m, 1H), 1.45 (s, 9H).

Z-Gly-Glu-O$^t$Bu (1.7 g, 4.3 mmol) was dissolved in 1,4-dioxane (15 ml) and under N$_2$ 10% palladium black (0.6 g) was added. The mixture was hydrogenated at atmospheric pressure for 5 hours. The mixture was filtered and the palladium was stirred with water (200 ml) for 2 hours, filtered and the filtrate was lyophilized. This afforded 0.65 g (58%) of H-Gly-Glu-O$^t$Bu.

$^1$H-NMR (DMSO-d$_6$), selected peaks, δ: 8.31 (d, 1H), 2.20 (t, 2H), 1.91 (m, 1H), 1.80 (m, 1H), 1.40 (s, 9H).

H-Gly-Glu-O$^t$Bu (0.15 g, 0.58 mmol) was suspended in DMF (5 ml) and DIEA (0.15 ml, 0.86 mmol) and succinimidyl tert-butyl octadecandioate (0.27 g, 0.58 mmol) were added and the resulting mixture was stirred at room temperature for 16 hours. AcOEt (50 ml) was added and the mixture was washed with 0.2N hydrochloric acid (100 ml) and water (3×100 ml). The organic phase was dried (Na$_2$SO$_4$) and concentrated in vacuo to afford 0.34 g (quant.) of tert-butyl octadecandioyl-Gly-Glu-O$^t$Bu.

$^1$H-NMR (CDCl$_3$), δ: 7.11 (d, 1H), 6.55 (t, 1H), 4.55 (dt, 1H), 4.00 (dq, 2H), 2.40 (t, 2H), 2.26 (t, 2H), 2.20 (t, 4H), 2.00 (m, 1H), 1.57-1.65 (m, 5H), 1.47 (s, 9H), 1.44 (s, 9H), 1.25 ("s", 22H, overlap with HDO).

Tert-butyl octadecandioyl-Gly-Glu-O$^t$Bu (0.32 g, 0.52 mmol) was dissolved in THF (5 ml) and added DIEA (0.11 ml, 0.63 mmol) and TSTU (0.19 g, 0.63 mmol) and the resulting mixture was stirred at room temperature under N$_2$ for 3 days. AcOEt (100 ml) was added and the mixture was washed with 0.15N hydrochloric acid (100 ml) and water (3×100 ml). The organic phase was dried (Na$_2$SO$_4$) and concentrated in vacuo to afford 0.3 g (81%) of tert-butyl octadecandioyl-Gly-Glu(OSu)-O$^t$Bu.

$^1$H-NMR (CDCl$_3$), selected peaks, δ: 6.89 (d, 1H), 6.44 (t, 1H), 4.60 (m, 1H), 3.95 (dq, 2H), 2.86 (s, 4H), 2.68 (q, 2H), 2.24 (t, 2H), 2.20 (t, 4H), 1.57-1.65 (m, 5H), 1.48 (s, 9H), 1.44 (s, 9H), 1.25 ("s", 22H, overlap with HDO).

Example 36

Synthesis of N$^{εB29}$—[N—(HOOC(CH$_2$)$_{14}$CO)—N-(2-carboxyethyl)-β-Ala] des B30 Human Insulin This compound was prepared in analogy with example 1, via coupling of 15-[[2-(2,5-dioxo-pyrrolidin-1-yloxycarbonyl)-ethyl]-(2-methoxycarbonyl-ethyl)-carbamoyl]-pentadecanoic acid methyl ester with Des(B30) human insulin and deprotection by NaOH.

LC-MS: M+4. 1530.3, calculated 1529.5

Preparation of methyl hexadecandioyl N-(2-(methoxycarbonyl)ethyl)-β-Ala-OSu

Hβ-Ala-OMe hydrochloride (5.45 g, 39 mmol) was dissolved in DMSO (100 ml) and tert-butyl acrylate (5.71 ml, 39 mmol) and DIEA (13.4 ml, 78 mmol) were added, and the resulting mixture was stirred at room temperature for 6 days. The mixture was partitioned between water (500 ml) and AcOEt (2×250 ml). The combined organic phases were washed with saturated aqueous NH$_4$Cl, dried (MgSO$_4$) and concentrated in vacuo. This afforded 7.24 g (80%) of N-(2-(methoxycarbonyl)ethyl)-β-Ala-OtBu.

$^1$H-NMR (CDCl$_3$) δ: 3.58 (s, 3H), 2.72 (t, 2H), 2.67 (t, 2H), 2.41 (t, 2H), 2.29 (t, 2H), 1.39 (s, 9H).

Hexadecanedioic acid monomethyl ester (150 mg, 0.5 mmol) was dissolved in DMF (5 mL). HOAt (102 mg, 0.75 mmol) and EDAC (143 mg, 0.75 mmol) was added and the reaction was stirred at 50° C. for 1 hour. After cooling to room temperature, DIEA (0.256 mL, 1.5 mmol) and N-(2-(methoxycarbonyl)ethyl)-β-Ala-OtBu (139 mg, 0.6 mmol) was added. The reaction was stirred overnight at room temperature. The mixture was partitioned between water (2×50 mL) and AcOEt (100 mL). The organic phase was dried (Na$_2$SO$_4$) and concentrated in vacuo to an oil. DCM (10 mL) and TFA (10 mL) was added and the mixture was stirred for 1 hour at room temperature, solvent removed in vacuo to afford 170 mg (87%) of methyl hexadecandioyl N-(2-(methoxycarbonyl)ethyl-β-Ala-OH.

LC-MS: 458 (M+1).

Methyl hexadecandioyl N-(2-(methoxycarbonyl)ethyl-β-Ala-OH (161 mg, 0.351 mmol) was dissolved in THF (10 mL) DIEA (0.073 mL, 0.42 mmol) and TSTU (127 mg, 0.42 mmol) was added. The mixture was stirred while cooled on an icebath for 30 min, followed by stirring for 2 hours at room temperature. The mixture was partitioned between and AcOEt (100 mL) and aqueous HCl (0.2 N, 2×80 mL). The organic phase was dried ($Na_2SO_4$) and concentrated in vacuo. This afforded 140 mg (72%) of methyl hexadecandioyl N-(2-(methoxycarbonyl)ethyl)-β-Ala-OSu as an oil.

LC-MS: 555 (M+1).

Example 37

Synthesis of $N^{\epsilon B29}$—[N—(HOOC($CH_2$)$_{16}$CO)—N-(2-carboxyethyl)-β-Ala] des B30 Human Insulin This compound was prepared in analogy with example 1 and 36 via coupling of methyl octadecandioyl N-(2-(methoxycarbonyl)ethyl)-β-Ala-OSu with Des(B30) human insulin and deprotection by NaOH.

Preparation of Methyl Octadecandioyl N-(2-(methoxycarbonyl)ethyl)-β-Ala-OSu

This compound was synthesized in analogy with methyl hexadecandioyl N-(2-(methoxycarbonyl)ethyl)-β-Ala-OSu using octadecanedioic acid mono methyl ester.

MALDI-TOF MS: Calculated 6146; found: 6151
LC-MS: 583 (M+1)

Pharmacological Methods

Assay (I)

Insulin Receptor Binding of the Insulin Derivatives of the Invention

The affinity of the insulin analogues of the invention for the human insulin receptor was determined by a SPA assay (Scintillation Proximity Assay) microtiterplate antibody capture assay. SPA-PVT antibody-binding beads, anti-mouse reagent (Amersham Biosciences, Cat No. PRNQ0017) were mixed with 25 ml of binding buffer (100 mM HEPES pH 7.8; 100 mM sodium chloride, 10 mM $MgSO_4$, 0.025% Tween-20). Reagent mix for a single Packard Optiplate (Packard No. 6005190) is composed of 2.4 μl of a 1:5000 diluted purified recombinant human insulin receptor—exon 11, an amount of a stock solution of A14 Tyr[$^{125}$I]-human insulin corresponding to 5000 cpm per 100 μl of reagent mix, 12 μl of a 1:1000 dilution of F12 antibody, 3 ml of SPA-beads and binding buffer to a total of 12 ml. A total of 100 μl was then added and a dilution series is made from appropriate samples. To the dilution series was then added 100 μl of reagent mix and the samples were incubated for 16 hours while gently shaken. The phases were the then separated by centrifugation for 1 min and the plates counted in a Topcounter. The binding data were fitted using the nonlinear regression algorithm in the GraphPad Prism 2.01 (GraphPad Software, San Diego, Calif.).

Preparation of Monoclonal mIR Antibodies

Specific antibodies (F12) were produced by monoclonal technique: RBF mice were immunized by injecting 50 μg of purified mIR in FCA subcutaneously followed by two injections with 20 μg of mIR in FIA. Highresponder mice were boosted intravenously with 25 μg of mIR and the spleens were harvested after 3 days. Spleen cells were fused with the myeloma Fox cell line (Köhler, G & Milstein C. (1976), European J. Immunology, 6:511-19; Taggart R T et al (1983), Science 219:1228-30). Supernatants were screened for antibody production in a mIR specific ELISA. Positive wells were cloned and tested in Western blotting.

TABLE 2

| Product | Receptor binding (% of human insulin) |
|---|---|
| Human insulin | 100 |
| $N^{\epsilon B29}$—(N—HOOC($CH_2$)$_{14}$CO-γ-Glu) des(B30) human insulin | 26 |
| $N^{\epsilon B29}$—(N—HOOC($CH_2$)$_{16}$CO-γ-Glu) des(B30) human insulin | 9.2 |
| $N^{\epsilon B29}$—(N—HOOC($CH_2$)$_{16}$CO-γ-Glu-N-(γ-Glu) des(B30) human insulin | 11 |
| $N^{\epsilon B29}$—(N-(Asp-OC($CH_2$)$_{16}$CO)-γ-Glu) des(B30) human insulin | 13 |
| $N^{\epsilon B29}$—(N-(Glu-OC($CH_2$)$_{14}$CO-γ-Glu) des(B30) human insulin | 13 |
| $N^{\epsilon B29}$—(N—HOOC($CH_2$)$_{14}$CO-) des(B30) human insulin | 9.4 |
| $N^{\epsilon B29}$—(N—HOOC($CH_2$)$_{16}$CO-α-Glu)-N-(β-Glu) des(B30) human insulin | 11 |
| $N^{\epsilon B29}$—(N-(Gly-OC($CH_2$)$_{13}$CO-γ-Glu) des(B30) human insulin | 22 |
| $N^{\epsilon B29}$—(N-(Sar-OC($CH_2$)$_{13}$CO-γ-Glu) des(B30) human insulin | 20 |
| $N^{\epsilon B29}$—(N—HOOC($CH_2$)$_{16}$CO-α-L-Asp)-N-(β-L-Asp) des(B30) human insulin | 14 |
| $N^{\epsilon B29}$—(N-(Gly-OC($CH_2$)$_{14}$CO-γ-Glu) des(B30) human insulin | 32 |
| $N^{\epsilon B29}$—(N-(Gly-OC($CH_2$)$_{15}$CO-γ-Glu) des(B30) human insulin | 4 |
| $N^{\epsilon B29}$—(N—HOOC($CH_2$)$_{14}$CO-β-L-Asp) des(B30) human insulin | 16 |
| 0525 $N^{\epsilon B29}$—(N—HOOC($CH_2$)$_{14}$CO-β-D-Asp) des(B30) human insulin | 37 |
| $N^{\epsilon B29}$—(N—HOOC($CH_2$)$_{13}$CO-β-L-Glu) des(B30) human insulin | 15 |
| $N^{\epsilon B29}$—(N—HOOC($CH_2$)$_{13}$CO-β-L-Asp) des(B30) human insulin | 11 |
| $N^{\epsilon B29}$—(N—HOOC($CH_2$)$_{16}$CO-δ-L-Aad) des(B30) human insulin | 7 |
| $N^{\epsilon B29}$—(N—HOOC($CH_2$)$_{16}$CO-γ-D-Glu) des(B30) human insulin | 13 |
| $N^{\epsilon B29}$—(N—HOOC($CH_2$)$_{15}$CO-β-L-Asp) des(B30) human insulin | 5.4 |
| $N^{\epsilon B29}$—(N—HOOC($CH_2$)$_{16}$CO-α-L-Asp) des(B30) human insulin | 13 |
| $N^{\epsilon B29}$—(N—HOOC($CH_2$)$_{16}$CO-α-L-Glu) des(B30) human insulin | 16 |

TABLE 2-continued

| Product | Receptor binding (% of human insulin) |
|---|---|
| $N^{\epsilon B29}$—(N—(HOOC(CH$_2$)$_{14}$CO-$\epsilon$-L-LysCO—) des(B30) human insulin | 5.7 |
| $N^{\epsilon B29}$—(N—HOOC(CH$_2$)$_{16}$CO-$\beta$-L-Asp) des(B30) human insulin | 11 |
| $N^{\epsilon B29}$—(N—(Gly-OC(CH$_2$)$_{16}$CO-$\gamma$-L-Glu) des(B30) human insulin | 9.1 |
| $N^{\epsilon B29}$—[N—(HOOC(CH$_2$)$_{16}$CO)-N-(carboxymethyl)-$\beta$-Ala] des(B30) human insulin | 9.4 |
| $N^{\epsilon B29}$—[N$^\alpha$—(HOOC(CH$_2$)$_{11}$)NHCO(CH$_2$)$_3$CO)-$\gamma$-L-Glu] des(B30) human insulin | 46 |

Assay (II)

Potency of the Insulin Derivatives of the Invention Relative to Human Insulin

Sprague Dawley male rats weighing 238-383 g on the experimental day were used for the clamp experiment. The rats had free access to feed under controlled ambient conditions and were fasted overnight (from 3 pm) prior to the clamp experiment.

Experimental Protocol

The rats were acclimatized in the animal facilities for at least 1 week prior to the surgical procedure. Approximately 1 week prior to the clamp experiment Tygon catheters were inserted under halothane anaesthesia into the jugular vein (for infusion) and the carotid artery (for blood sampling) and exteriorised and fixed on the back of the neck. The rats were given Streptocilin vet. (Boehringer Ingelheim; 0.15 ml/rat, i.m.) post-surgically and placed in an animal care unit (25° C.) during the recovery period. In order to obtain analgesia, Anorphin (0.06 mg/rat, s.c.) was administered during anaesthesia and Rimadyl (1.5 mg/kg, s.c.) was administered after full recovery from the anaesthesia (2-3 h) and again once daily for 2 days.

The clamp technique employed was adapted from (1). At 7 am on the experimental day overnight fasted (from 3 pm the previous day) rats were weighed and connected to the sampling syringes and infusion system (Harvard 22 Basic pumps, Harvard, and Perfectum Hypodermic glass syringe, Aldrich) and then placed into individual clamp cages where they rested for ca. 45 min before start of experiment. The rats were able to move freely on their usual bedding during the entire experiment and had free access to drinking water. After a 30 min basal period during which plasma glucose levels were measured at 10 min intervals, the insulin derivative to be tested and human insulin (one dose level per rat, n=6-7 per dose level) were infused (i.v.) at a constant rate for 300 min. Plasma glucose levels were measured at 10 min intervals throughout and infusion of 20% aqueous glucose was adjusted accordingly in order to maintain euglyceamia. Samples of re-suspended erythrocytes were pooled from each rat and returned in about ½ ml volumes via the carotid catheter.

On each experimental day, samples of the solutions of the individual insulin derivatives to be tested and the human insulin solution were taken before and at the end of the clamp experiments and the concentrations of the peptides were confirmed by HPLC. Plasma concentrations of rat insulin and C-peptide as well as of the insulin derivative to be tested and human insulin were measured at relevant time points before and at the end of the studies. Rats were killed at the end of experiment using a pentobarbital overdose.

Test compounds and doses: Insulins to be tested were diluted from a stock solution containing 97 μM of the insulin derivative in 5 mM phosphate pH 7.7. The final concentration in the solution ready for use was 0.45 μM of the insulin derivative, 5 mM of phosphate, 100 mM of sodium chloride, 0.007% of polysorbate 20. The pH was 7.7 and the i.v. infusion rate was 15 and 20 pmol·min$^{-1}$·kg$^{-1}$.

A stock solution of human insulin that was used as reference compound was formulated in a similar medium and infused i.v. at 6, 15 or 30 pmol·min$^{-1}$·kg$^{-1}$.

Both stock solutions were stored at −20° C. and thawed overnight at 4° C. before use. The solutions were gently turned upside down several times 15 min before they were transferred to the infusion syringes.

TABLE 3

| Insulin derivative | Potency relative to human insulin |
|---|---|
| $N^{\epsilon B29}$—(N—HOOC(CH$_2$)$_{14}$CO-$\gamma$-Glu) des(B30) human insulin | >50% |
| $N^{\epsilon B29}$—(N—HOOC(CH$_2$)$_{16}$CO-$\gamma$-Glu) des(B30) human insulin | >50% |
| $N^{\epsilon B29}$—(N—HOOC(CH$_2$)$_{16}$CO-$\gamma$-Glu-N-($\gamma$-Glu) des(B30) human insulin | >50% |
| $N^{\epsilon B29}$—(N—HOOC(CH$_2$)$_{14}$CO-$\beta$-L-Asp) des(B30) human insulin | >50% |
| $N^{\epsilon B29}$—(N-(Gly-OC(CH$_2$)$_{14}$CO-$\gamma$-Glu) des(B30) human insulin | >50% |
| $N^{\epsilon B29}$—(N—HOOC(CH$_2$)$_{14}$CO-$\beta$-L-Asp) des(B30) human insulin | >50% |

Assay (III)

Determination in pigs of $T_{50\%}$ of the Insulin Derivatives of the Invention $T_{50\%}$ is the time when 50% of an injected amount of the A14 Tyr[$^{125}$I] labelled derivative of an insulin to be tested has disappeared from the injection site as measured with an external γ-counter.

The principles of laboratory animal care were followed, Specific pathogen-free LYYD, non-diabetic female pigs, cross-breed of Danish Landrace, Yorkshire and Duroc, were used (Holmeniund, Haarloev, Denmark) for pharmacokinetic and pharmacodynamic studies. The pigs were conscious, 4-5 months of age and weighing 70-95 kg. The animals were fasted overnight for 18 h before the experiment.

Formulated preparations of insulin derivatives labelled in Tyr$^{414}$ with $^{125}$I were injected sc. in pigs as previously described (Ribel, U., Jorgensen, K, Brange, J, and Henriksen, U. The pig as a model for subcutaneous insulin absorption in man. Serrano-Rios, M and Lefèbvre, P. J. 891-896. 1985. Amsterdam; New York; Oxford, Elsevier Science Publishers. 1985 (Conference Proceeding)).

At the beginning of the experiments a dose of 60 nmol of the insulin derivative according to the invention (test compound) and a dose of 60 nmol of insulin detemir (both $^{125}$I labelled in Tyr A14) were injected at two separate sites in the neck of each pig.

The disappearance of the radioactive label from the site of sc. injection was monitored using a modification of the traditional external gamma-counting method (Ribel, U. Subcutaneous absorption of insulin analogues. Berger, M. and Gries, F. A. 70-77 (1993). Stuttgart; New York, Georg Thime Verlag (Conference Proceeding)). With this modified method it was possible to measure continuously the disappearance of radioactivity from a subcutaneous depot for several days using cordless portable device (Scancys Laboratorieteknik, Værløse, DK-3500, Denmark). The measurements were performed at 1-min intervals, and the counted values were corrected for background activity.

In Table 4, the column "test/detemir" shows the $T_{50\%}$ found for each of the compounds tested ("test") and the $T_{50\%}$ found for insulin detemir ("detemir") in the same experiment.

TABLE 4

| Insulin derivative | $T_{50\%}$, hours test/detemir |
|---|---|
| $N^{\epsilon B29}$—(N—HOOC(CH$_2$)$_{14}$CO-γ-Glu) des(B30) human insulin | 9.0/9.5 |
| $N^{\epsilon B29}$—(N—HOOC(CH$_2$)$_{16}$CO-γ-Glu) des(B30) human insulin | 10.6/9.7 |
| $N^{\epsilon B29}$—(N—HOOC(CH$_2$)$_{16}$CO-γ-Glu-N-(γ-Glu) des(B30) human insulin | 7.8/7.4 |
| $N^{\epsilon B29}$—(N-(Asp-OC(CH$_2$)$_{16}$CO)-γ-Glu) des(B30) human insulin | 3.5/7.4 |
| $N^{\epsilon B29}$—(N-(Asp-OC(CH$_2$)$_{16}$CO—) des(B30) human insulin | 4.1/7.4 |
| $N^{\epsilon B29}$—(N—HOOC(CH$_2$)$_{16}$CO-α-Glu)-N-(β-Asp) des(B30) human insulin | 8.7/9.1 |

The invention claimed is:

1. An insulin derivative which is a naturally occurring insulin or an analogue thereof which has a side chain attached to the α-amino group of the N-terminal amino acid residue of the B chain or to the ε-amino group of a Lys residue present in the B chain of the parent insulin, the side chain being of the general formula:

-W-X—Y-Z wherein W is:
   an α-amino acid residue having a carboxylic acid group in the side chain which amino acid is selected from the group consisting of α-Asp, β-Asp, α-Glu, γ-Glu, α-hGlu and δ-hGlu and which residue forms, with one of its carboxylic acid groups, an amide group together with the α-amino group of the N-terminal amino acid residue of the B chain or together with the ε-amino group of a Lys residue present in the B chain of the parent insulin;

X is:
   —CO—;
Y is:
   —(CH$_2$)$_m$— where m is an integer in the range of 6 to 32;
Z is:
   —COOH;
and any Zn$^{2+}$ complexes thereof.

2. An insulin derivative according to claim 1, wherein side chain -W-X—Y-Z is attached to the ε-amino group of a Lys residue present in the B chain of the parent insulin.

3. An insulin derivative according to claim 1, wherein Y is —(CH$_2$)$_m$— where m is an integer in the range of from 12-16.

4. An insulin derivative according to claim 1, wherein the parent insulin is; des(B30) human insulin.

5. An insulin derivative according to claim 1, wherein the insulin derivative is $N^{\epsilon B29}$—(N$^\alpha$—(HOOC(CH$_2$)$_{14}$CO)-γ-Glu) des(B30) human insulin.

6. A zinc complex of an insulin derivative according to claim 1, wherein each insulin hexamer in said complex binds two zinc ions.

7. A zinc complex of an insulin derivative according to claim 1, wherein each insulin hexamer in said complex binds three zinc ions.

8. A zinc complex of an insulin derivative according to claim 1, wherein each insulin hexamer in said complex binds four zinc ions.

9. A pharmaceutical composition for the treatment of diabetes in a patient in need of such treatment, said composition comprising a therapeutically effective amount of an insulin derivative according to claim 1 together with a pharmaceutically acceptable carrier.

10. A pharmaceutical composition for the treatment of diabetes in a patient in need of such treatment, said composition comprising a therapeutically effective amount of an insulin derivative according to claim 1 in mixture with an insulin or an insulin analogue which has a rapid onset of action, together with a pharmaceutically acceptable carrier.

11. A pharmaceutical composition for the treatment of diabetes in a patient in need of such treatment, said composition comprising a therapeutically effective amount of an insulin derivative with a pharmaceutically acceptable carrier, wherein said insulin derivative is $N^{\epsilon B29}$—(N$^\alpha$—(HOOC(CH$_2$)$_{14}$CO)-γ-Glu) des(B30) human insulin.

12. A pharmaceutical composition for the treatment of diabetes in a patient in need of such treatment, said composition comprising a therapeutically effective amount of an insulin derivative in mixture with an insulin or an insulin analogue which has a rapid onset of action, together with a pharmaceutically acceptable carrier, wherein said insulin derivative is $N^{\epsilon B29}$—(N$^\alpha$—(HOOC(CH$_2$)$_{14}$CO)—γ-Glu) des(B30) human insulin.

* * * * *

UNITED STATES PATENT AND TRADEMARK OFFICE
CERTIFICATE OF CORRECTION

| | |
|---|---|
| PATENT NO. | : 7,615,532 B2 |
| APPLICATION NO. | : 11/343005 |
| DATED | : November 10, 2009 |
| INVENTOR(S) | : Jonassen et al. |

It is certified that error appears in the above-identified patent and that said Letters Patent is hereby corrected as shown below:

On the title page item [75], should read as follows

Ib Jonassen, Valby (DK);

Thomas Hoeg-Jensen, Klampenborg (DK);

Svend Havelund, Bagsvaerd (DK);

Ulla Ribel-Madsen, Virum (DK)

Signed and Sealed this
First Day of March, 2016

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 7,615,532 B2 | Page 1 of 1 |
| APPLICATION NO. | : 11/343005 | |
| DATED | : November 10, 2009 | |
| INVENTOR(S) | : Jonassen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 307 days.

Signed and Sealed this
Seventh Day of June, 2016

Michelle K. Lee
*Director of the United States Patent and Trademark Office*